(12) United States Patent
Alphandery et al.

(10) Patent No.: US 10,391,122 B2
(45) Date of Patent: Aug. 27, 2019

(54) NON-PYROGENIC PREPARATION COMPRISING NANOPARTICLES SYNTHESIZED BY MAGNETOTACTIC BACTERIA FOR MEDICAL OR COSMETIC APPLICATIONS

(71) Applicant: NANOBACTERIE, Paris (FR)

(72) Inventors: Edouard Alphandery, Paris (FR); Mickael Durand-Dubief, Garches (FR)

(73) Assignee: NANOBACTERIE, Paris (FR)

( * ) Notice: Subject to any disclaimer, the term of this patent is extended or adjusted under 35 U.S.C. 154(b) by 0 days.

(21) Appl. No.: 15/510,048

(22) PCT Filed: Jun. 15, 2016

(86) PCT No.: PCT/FR2016/000095
§ 371 (c)(1),
(2) Date: Mar. 9, 2017

(87) PCT Pub. No.: WO2016/203121
PCT Pub. Date: Dec. 22, 2016

(65) Prior Publication Data
US 2017/0296580 A1    Oct. 19, 2017

(30) Foreign Application Priority Data
Jun. 17, 2015  (FR) .................................... 15 01267

(51) Int. Cl.
| | | |
|---|---|---|
| *A61K 33/26* | (2006.01) | |
| *A61K 41/00* | (2006.01) | |
| *C01G 49/08* | (2006.01) | |
| *A61K 8/02* | (2006.01) | |
| *A61K 8/19* | (2006.01) | |
| *A61K 8/25* | (2006.01) | |
| *A61K 8/26* | (2006.01) | |
| *A61K 8/365* | (2006.01) | |
| *A61K 8/49* | (2006.01) | |
| *A61K 8/55* | (2006.01) | |
| *A61K 8/73* | (2006.01) | |
| *A61K 8/85* | (2006.01) | |
| *A61K 8/99* | (2017.01) | |
| *A61K 9/51* | (2006.01) | |
| *A61K 35/74* | (2015.01) | |
| *A61K 49/18* | (2006.01) | |
| *A61L 31/02* | (2006.01) | |
| *A61L 31/08* | (2006.01) | |
| *A61L 31/10* | (2006.01) | |
| *A61Q 19/00* | (2006.01) | |
| *G01N 33/84* | (2006.01) | |

(52) U.S. Cl.
CPC ............ *A61K 33/26* (2013.01); *A61K 8/0245* (2013.01); *A61K 8/19* (2013.01); *A61K 8/25* (2013.01); *A61K 8/26* (2013.01); *A61K 8/365* (2013.01); *A61K 8/4953* (2013.01); *A61K 8/55* (2013.01); *A61K 8/553* (2013.01); *A61K 8/73* (2013.01); *A61K 8/736* (2013.01); *A61K 8/85* (2013.01); *A61K 8/99* (2013.01); *A61K 9/5115* (2013.01); *A61K 9/5123* (2013.01); *A61K 9/5146* (2013.01); *A61K 9/5153* (2013.01); *A61K 9/5161* (2013.01); *A61K 9/5176* (2013.01); *A61K 35/74* (2013.01); *A61K 41/0052* (2013.01); *A61K 49/183* (2013.01); *A61K 49/1827* (2013.01); *A61K 49/1836* (2013.01); *A61K 49/1839* (2013.01); *A61K 49/1842* (2013.01); *A61K 49/1857* (2013.01); *A61K 49/1863* (2013.01); *A61L 31/028* (2013.01); *A61L 31/08* (2013.01); *A61L 31/086* (2013.01); *A61L 31/088* (2013.01); *A61L 31/10* (2013.01); *A61Q 19/00* (2013.01); *C01G 49/08* (2013.01); *G01N 33/84* (2013.01); *A61K 2800/10* (2013.01); *A61K 2800/413* (2013.01); *A61K 2800/62* (2013.01); *A61K 2800/621* (2013.01); *A61K 2800/622* (2013.01); *A61K 2800/624* (2013.01); *A61K 2800/651* (2013.01); *A61L 2300/102* (2013.01); *C01P 2004/50* (2013.01); *C01P 2004/62* (2013.01); *C01P 2004/64* (2013.01); *C01P 2004/80* (2013.01); *C01P 2006/42* (2013.01); *G01N 2333/195* (2013.01)

(58) Field of Classification Search
None
See application file for complete search history.

(56) References Cited

FOREIGN PATENT DOCUMENTS

| GB | 2 464 998 A | 5/2010 |
|---|---|---|
| WO | 2011/061259 A1 | 5/2011 |

OTHER PUBLICATIONS

By Xie et al. (Production, Modification, and Bio-Applications of Magnetic Nanoparticles Gestated by Margnetotactic bacteria, Nano Res (2009) 2: 261-278). (Year: 2009).*
Gao et al. (Pullulan Acetate Coated Magnetite Nanoparticles for HyperThermia: Preparation, Characterization and In Vitro Experiments, Nano Res (2010) 3: 23-31). (Year: 2010).*
Xie et al. (Production, Modification, and Bio-Applications of Magnetic Nanoparticles Gestated by Magnetotactic bacteria, Nano Res (2009) 2: 261-278). (Year: 2009).*
Jin Xie et al.: "Production, Modification and Bio-Applications of Magnetic Nanoparticles Gestated by Magnetotactic Bacteria", Dec. 31, 2009 (Dec. 31, 2009), XP055261235.
(Continued)

*Primary Examiner* — Robert A Wax
*Assistant Examiner* — Melissa S Mercier
(74) *Attorney, Agent, or Firm* — Maier & Maier, PLLC

(57) ABSTRACT

A non-pyrogenic preparation containing nanoparticles synthesized by magnetotactic bacteria for medical or cosmetic applications. The nanoparticles are constituted by a crystallized mineral central part including predominantly an iron oxide, as well as a surrounding coating without material from the magnetotactic bacteria.

23 Claims, No Drawings

(56) References Cited

OTHER PUBLICATIONS

Fuping Gao et al.: "Pullulan acetate coated magnetite nanoparticles for hyper-thermia: Preparation, characterization and in vitro experiments", NANO Research, vol. 3, No. 1, Jan. 1, 2010 (Jan. 1, 2010), CN, pp. 23-31, XP055261219, ISSN: 1998-0124, DOI: 10.1007/s12274-010-1004-6.
Alphandery et al., Acsnano, V., vol. 5, 2011, pp. 6279.
International Search Report, dated Nov. 16, 2016, from corresponding PCT application.

* cited by examiner

NON-PYROGENIC PREPARATION COMPRISING NANOPARTICLES SYNTHESIZED BY MAGNETOTACTIC BACTERIA FOR MEDICAL OR COSMETIC APPLICATIONS

FIELD OF THE INVENTION

The present invention relates to synthetic nanoparticles of bacterial origin, modified, useful in medicine or in cosmetics.

STATE OF THE ART

Magnetotactic bacteria synthesize iron oxide nanoparticles, called magnetosomes, which possess outstanding properties due on the one hand to the presence of a crystallized mineral central part of large size, typically of the order of 20 to 120 nm in diameter leading to advantageous ferrimagnetic properties, and on the other hand to their arrangement in chains that prevents magnetosome aggregation. These nanoparticles of bacterial origin display advantageous magnetic properties compared to nanoparticles resulting from chemical synthesis. For example, for an equivalent concentration in iron and when they are exposed to the application of an alternating magnetic field, suspensions of magnetosome chains extracted from magnetotactic bacteria produce more heat than chemical nanoparticles commonly used for magnetic hyperthermia such as chemical superparamagnetic iron oxide nanoparticles (SPION) and chemical ferrimagnetic iron oxide nanoparticles (FION). When such suspensions are administered to breast cancer tumors xeno-grafted under the skin of mice and exposed to several applications of an alternating magnetic field, this induces anti-tumor activity (Alphandéry et al., AcsNano, V. 5, P. 6279 (2011)). In addition, for an equivalent concentration in iron, this anti-tumor activity is larger than that observed with SPION or FION.

However, these chains of magnetosomes come from gram negative bacteria and can therefore possess in some cases a high endotoxin concentration as well as biological material, which is difficult to precisely characterize. The present invention therefore aims to provide a method of magnetosome production that enables to overcome these problems.

DESCRIPTION

The present invention results from the unexpected demonstration, by the inventors, that it was possible to replace the natural coating of the magnetosomes with another coating to yield non-pyrogenic synthetic nanoparticles, which can be used in health, diagnosis and/or cosmetics.

Thus, the present invention relates to a preparation comprising at least one synthetic nanoparticle, wherein the nanoparticle comprises:

A crystallized mineral central part comprising predominantly an iron oxide, synthesized by a living organism, and A surrounding coating comprising no material originating from the living organism.

The preparation according to the invention can comprise at least 1, 2, 3, 5, 10, 100, $10^3$, $10^4$, $10^5$, $10^6$, $10^7$, $10^8$, $10^9$ synthetic nanoparticles comprised in a volume of 1 µm$^3$, 1 mm$^3$, or 1 dm$^3$. It may be a suspension of synthetic nanoparticles, preferentially comprised in a liquid medium, or it may be an assembly of synthetic nanoparticles comprised in a liquid, solid or gaseous medium.

The present invention also relates to a crystallized central part predominantly comprising an iron oxide synthesized by a living organism, and not comprising any coating.

A synthetic nanoparticle is a particle whose size is in at least one dimension lower than 10, 5, 2, 5 or 1 µm, preferentially lower than 750, 500, 400 or 300 nm, most preferentially lower than 200 or 100 nm, which is preferentially in a solid state and whose size is notably measurable by transmission electron microscopy (TEM). The word "synthetic" indicates that the nanoparticle has been manufactured using at least one step involving man, in particular using biological or chemical processes.

The synthetic nanoparticle according to the invention can possess at least one magnetic property, such as:

be diamagnetic, superparamagnetic, preferentially ferrimagnetic or ferromagnetic, possess at least one magnetic domain, possess at least one non-zero magnetic moment, possess a coercivity larger than 0.5, 1, 10, 100, or 1000 Oe at a temperature above 0, 10, 100, 273, 310, 373, or 1000 K, or possess a ratio between remanant and saturating magnetization, which is larger than 0.01, 0.1, 0.2, 0.5, 0.7, 0.9, 0.95, or 0.99 at temperature larger than 0, 10, 100, 273, 310, 373, or 1000 K, these properties being preferentially due to the properties of its central part.

The synthetic nanoparticle according to the invention is preferentially a nanoparticle possessing a single magnetic domain, which can lead to better magnetic properties compared with nanoparticles having several magnetic domains.

The synthetic nanoparticle according to the invention is preferentially a ferrimagnetic or ferromagnetic nanoparticle, in particular a nanoparticle whose magnetic moment is thermally stable at physiological temperature and/or whose size is larger than 1, 2, 5, 10, 15, 20, 25, 30, 35, 40, 45, 50, 55, 60, 70, 80, 90, 100, 150, 200, 500 or 1000 nm.

The synthetic nanoparticle according to the invention may be a superparamagnetic nanoparticle, in particular a nanoparticle whose magnetic moment is thermally unstable at physiological temperature and/or whose size is lower than 1, 2, 5, 10, 15, 20, 25, 30, 35, 40, 45, 50, 55, 60, 70, 80, 90, 100, 150, 200, 500 or 1000 nm.

The average diameter of the synthetic nanoparticle according to the invention can be measured using transmission electron microscopy (TEM) or with the help of a dynamic or non-dynamic light scattering method.

The central part of the synthetic nanoparticle predominantly comprises an iron oxide, i.e. at least 10 or 25%, preferentially at least 50, 75, 95, 97, 99, 99.5 or 99.9% of oxide of iron. This percentage of iron oxide corresponds in particular to the number of atoms comprised in the iron oxide of the central part divided by the number of atoms comprised in the iron oxide of the synthetic nanoparticle or to the mass of iron oxide comprised in the central part divided by the mass of iron oxide comprised in the synthetic nanoparticle.

Preferentially, the iron oxide is maghemite, magnetite or an intermediate composition between maghemite and magnetite.

Preferentially, the living organism synthesizing the central part of synthetic nanoparticles according to the invention is a eukaryotic cell or a bacterium, more preferentially a bacterium synthesizing magnetic nanoparticles, and even more preferentially a magnetotactic bacterium. Most preferentially, the bacteria according to the invention belong to the magnetotactic strains, in particular *Magnetospirillum*

*magneticum* AMB-1, *Magnetococcus marinus* sp. MC-1, *Magnetovirrium blakemorei* MV-1, MV-2 and MV-4, *Magnetospirillum magnetotacticum* MS-1, *Magnetospirillum gryphiswaldense* MSR-1, *Magnetospirillum magneticum* MGT-1, and *Desulfovibrio magneticus* RS-1.

One will also notice that the synthetic nanoparticle according to the invention differs from the magnetosomes extracted from the magnetotactic bacteria, usually arranged in chains, by the absence of organic material originating from magnetotactic bacteria in their coating. The coating preferentially does not comprise non-denatured organic material. Denaturation is defined here as the loss, by a biological macromolecule (e.g. nucleic acid or protein), of its usual three-dimensional conformation. The synthetic nanoparticle may indeed comprise, in its coating, denatured organic matter originating from magnetotactic bacteria. This denatured organic material may appear after a treatment intended to purify nanoparticles, such as a chemical, thermal or magnetic treatment or a combination of these treatments.

In one embodiment, the coating comprises less than 50%, 25%, 10%, or 1% of non-denatured organic material coming from magnetotactic bacteria, e.g. lipids, endotoxins and/or non-denatured proteins coming from magnetotactic bacteria. This percentage of non-denatured organic material corresponds in particular to the mass of this material comprised in the coating divided by the mass of the synthetic nanoparticle. This small quantity of organic material coming from bacteria can be characterized by a mass of chemical functional groups at the surface of or inside the purified central part, such as phosphates or amines, which is less than 1 mg, 0.1 mg, 0.01 mg, 0.001 mg, 0.0001 mg or 40 ng per 1 mg in total iron of the central part. This low quantity of non-denatured organic material can enable to produce a suspension of synthetic nanoparticles with a sufficiently low level of pyrogenicity according to the standards in force, in particular for allowing administration to a human or an animal.

In one embodiment, the preparation according to the invention comprises at least 2, 5, 10, 20, 30, 50, 100, 150, 200, 500, 10000, 50000 or 100000 synthetic nanoparticles which are bond to each other by connecting material. The connecting material may have at least one of the following properties: i), be made, at least in part, of the same material(s) as that(those) of the coating of the synthetic nanoparticles, ii), link at least two synthetic nanoparticles together, over a distance lower or larger than 1 mm, 100 µm, 10 µm, 1 µm, 100 nm, 50 nm, 40 nm, 30 nm, 20 nm, 10 nm, 5 nm, 2 nm, or 1 nm, iii), promote cellular internalization, iv), be positively or negatively charged or be neutral, v), have or not have a therapeutic or diagnostic effect, vi), be sufficiently resistant to ensure the between at least two synthetic nanoparticles either when the preparation is in a liquid, physical, gaseous, or biological medium, or after sterilization or after a physical, biological, or chemical treatment, for example with the help of the solution or medium used for the formulation of the preparation, notably for the administration to an organism, vii), comprise less than 20%, 15%, 10%, 5%, 2%, 1%, 0.1%, 0.01%, or 0.001% of carbonaceous material coming from the living organism, viii), not come from the living organism.

The synthetic nanoparticles may be arranged in a geometric figure which can be: a straight chain, a circle, a square, a rectangle, a triangle, a pentagon, a hexagon, a heptagon, an octagon, a polygon or a polyhedron. These figures can be observed by Transmission Electron Microscopy.

An arrangement of at least two synthetic nanoparticles according to a geometric figure can correspond to an arrangement of these nanoparticles having: i), crystallographic axes orientated in a preferential direction, ii), at least two sides or faces belonging to two different synthetic nanoparticles, which are parallel or perpendicular, or which form an angle larger or lower than 1, 2, 5, 10, 15, 20, 25, 30, 35, 40, 45, 50, 60, 70, 80, 90, 100, 150, 180, 225, 250, 300, 325, 350, or 379 degrees, iii), an alignment parallel to a magnetic field when these nanoparticles are exposed to the application of a magnetic field, in particular a field of larger intensity than $10^{-10}$ T, $10^{-9}$ T, $10^{-8}$ T, $10^{-7}$ T, $10^{-6}$ T, $10^{-5}$ T, $10^{-4}$ T, $10^{-3}$ T, $10^{-2}$ T, $10^{-1}$ T, 1 T or, iv), linking materials linking at least two synthetic nanoparticles together.

An arrangement of at least two synthetic nanoparticles within a geometric figure can be characterized by a variation of the zeta potential as a function of pH, which is a continuous variation such as a continuous decrease or increase, preferentially a continuous decrease, when the pH increases from 1 to 14, 2 to 12, 3 to 11, 4 to 10, 5 to 9, or 6 to 8, wherein a continuous decrease or increase may correspond to a variation measured between more than 1, 2, 3, 4, 5, 6, 7, 8, 9, 10, 11, 12, 13, 14 different pH units which is either a decrease or an increase.

In contrast, an arrangement of at least two synthetic nanoparticles, which is not in a geometric figure, such as an aggregate, can be characterized by a variation of zeta potential as a function of pH, which is a succession of at least 1, 2, 3, 4, 5, 7, 9, 10, 12, 15, 20 decrease(s) and increase(s) when the pH increases from 1 to 14, 2 to 12, 3 to 11, 4 to 10, 5 to 9, or 6 to 8.

An arrangement within a geometrical figure may take place in a solid, liquid or gaseous medium, i.e. in particular in a medium surrounding the synthetic nanoparticles, such as the medium used for the formulation of the synthetic nanoparticles or that surrounding these nanoparticles during their studies or characterizations.

According to the invention, it is preferred that when the living organism synthesizing the central part of the synthetic nanoparticles is a magnetotactic bacterium, the synthetic nanoparticles according to the invention comprise the central parts of the magnetosomes coated with a compound.

Preferentially, the central part of the synthetic nanoparticles according to the invention has at least one of the following properties:

($\alpha$), a crystalline part presenting at least 1, 2, 5, 10, 50, 100, 150 or 200 crystalline planes, being preferentially within a mineral form, comprising predominantly iron oxide, preferentially maghemite, notably when the central part is brought into contact with oxygen, magnetite, notably when the central part is not brought into contact with oxygen, or a mixture of maghemite and magnetite, ($\beta$), a ferrimagnetic or ferromagnetic behavior, notably at physiological temperatures, ($\chi$), a single magnetic domain, or magnetic monodomain, ($\delta$), a magnetic microstructure, which can be characterized by the presence of magnetic field lines that can be orientated in a preferential direction such as an easy magnetization axis or a crystallographic direction of the central part of the synthetic nanoparticles such as [111], where such magnetic microstructure may under certain conditions be observable, notably by electronic holography, ($\epsilon$), a size between 1 nm and 2 µm, 5 nm and 1 µm, 5 and 500 nm, 5 and 250 nm, 5 and 100 nm, 5 and 80 nm, 5 and 60 nm, 10 nm and 1 µm, 10 and 500 nm, 10 and 250 nm, 10 and 100 nm, 10 and 80 nm, 10 and 60 nm, 15 nm and 1 µm, 15 and 500 nm, 15 and 250 nm, 15 and 100 nm, 15 and 80 nm, 15 and 60 nm, 20 nm and 1 µm, 20 and 500 nm, 20 and 250 nm, 20 and 100 nm, 20 and 80 nm or 20 and 60 nm, ($\phi$), a size larger than 1, 2, 5, 10, 15, 20, 25, 30, 35 or 40 nm, ($\gamma$), a size lower than 2000, 1000, 500, 400, 300, 200, 150, 120, 100, 95, 90, 80, 75, 70, 65, 60, 55, 50, 45, 40, 35, 30, 25, 20, 15, 10 or 5 nm, ($\eta$), the possible presence of a zeta potential, a charge, a surface charge, ($\iota$), an isoelectric point, preferentially acidic of pH lower than or equal to 7, 6, 5, 4, 3, 2 or 1, ($\upsilon$), an isoelectric point, which is the closest to 7 when there remains the lowest quantity of organic material at the surface of the central part; when there remains a low quantity of organic material, the isoelectric point can be between pH 6.5 and pH 7.5, between pH 6.2 and pH 7.1, or between pH 6.1 and pH 7.1.

As will be understood by the person skilled in the art, the zeta potential, the charge, the surface charge usually depend on the pH, the salinity, the bacterial species synthesizing the central part of the synthetic nanoparticles, the aggregation state, the percentage of organic material at the surface of these central parts. They may be: (1), positive at acid pH, at pH equal to or lower than 7, 6, 5, 4, 3, 2, or 1, (2), negative at basic pH, at pH larger than or equal to 13, 12, 11, 10, 9, 8, 7, (3), vary as a function of pH within a range comprised between −10 and 10 mV, −20 and 20 mV, −30 and 30 mV, −40 and 40 mV, −50 and 50 mV, −60 and 60 mV, −70 and 70 mV, −80 and 80 mV, −90 and 90 mV, −100 and 100 mV, −150 and 150 mV, or −200 and 200 mV, (4), vary the most significantly as a function of pH values when the quantity of organic material, preferentially of carbonaceous material, remaining at the surface of the central parts of these synthetic nanoparticles, is the lowest.

Preferentially, the central part of the synthetic nanoparticles comprises less than 50, 25, 10, 5, 2, 1, 0.5, 0.2, 0.1, 0.05, 0.01 or 0.001% organic material. As used herein, this percentage of organic material represents the percentage in mass or in number of atoms or in volume of any chemical element or combination of chemical elements comprised in the organic material such as carbon, nitrogen, phosphorus. This percentage can be measured using instruments of elementary analysis such as total organic carbon (TOC) or carbon, hydrogen, nitrogen, sulfur, oxygen (CHNS/O) analyzers.

In one embodiment, the coating according to the invention, also designated as surrounding coating, is a solid, liquid or gaseous material, preferentially in the solid state, which surrounds the central part, notably in the form of a layer, crystallized or not, notably over a distance measured from the center of the central part which is lower than 100 µm, 10 µm, 5 µm, 1 µm, 500 nm, 250 nm, 100 nm, 10 nm, or 1 nm. This coating can in particular serve to stabilize the central part or to link the synthetic nanoparticles together.

The coating may have at least one property in common with the central part or at least one property different from the central part.

According to the invention, the surrounding coating preferentially does not comprise non-denatured material originating from the living organism. It may comprise less than 50, 40, 30, 20, 10, 5, 4, 3, 2, 1, 0.1, 0.05, 0.01, 0.001 or 0.0001% of this material. This percentage can be defined as the ratio between the number of atoms coming from the living organism comprised in the coating divided by the total number of atoms comprised in the coating or the ratio between the mass of atoms coming from the living organism comprised in the coating divided by the total mass of atoms comprised in the coating. This percentage can correspond to a percentage of carbonaceous or organic material.

The synthetic nanoparticle, according to the invention, is non-pyrogenic, wherein non-pyrogenicity can be defined by measuring the quantity of endotoxins per milligram of synthetic nanoparticle, preferentially comprised in 1 milliliter of the preparation, which is lower than or equal to $10^9$, $10^8$, $10^7$ or $10^6$, preferentially lower than or equal to $10^4$ or $10^3$, most preferentially lower than or equal to 100, 50, 10, 5 or 1 endotoxin unit (EU). As the man skilled in the art knows, 1 EU can correspond to a quantity of 100 µg per mL of endotoxins originating from *E-Coli*.

Preferentially, the synthetic nanoparticle is non-pyrogenic when its coating or its central part is non-pyrogenic, preferentially when its coating and its central part are non-pyrogenic, where non-pyrogenicity can in this case be defined by measuring the quantity of endotoxins per milligram of the central part and/or of the coating of the synthetic nanoparticle, preferentially comprised in 1 milliliter of the preparation, which is lower than or equal to $10^9$, $10^8$, $10^7$ or $10^6$, preferentially lower than or equal to $10^4$ or $10^3$, most preferentially lower than or equal to 100, 50, 10, 5 or 1 endotoxin unit (EU).

As used herein, a preparation is non-pyrogenic when substances other than the synthetic nanoparticles comprised in the preparation, such as the substances comprised in the excipient and/or the solvent of the preparation and/or the matrix surrounding the synthetic nanoparticles are non-pyrogenic.

Preferentially, the non-pyrogenic preparation is characterized by a percentage of endotoxins lower than or equal to 50, 20, 1, $10^{-1}$, $10^{-2}$, $10^{-3}$, $10^{-4}$, $10^{-5}$, $10^{-6}$, $10^{-7}$, $10^{-8}$ or $10^{-9}$%, where this percentage can be: (i), the mass of endotoxin divided by the total mass of the preparation, (ii), the volume occupied by the endotoxins divided by the total volume of the preparation, (iii), the number of atoms comprised in the endotoxins of the preparation divided by the total number of atoms comprised in the preparation.

Preferentially, the non-pyrogenic preparation is characterized by a quantity of endotoxins lower than or equal to $10^9$, $10^8$, $10^7$ or $10^6$, preferentially lower than or equal to $10^4$ or $10^3$, most preferentially lower than or equal to 100, 50, 10, 5 or 1 EU or EU per milligram of iron oxide or EU per milliliter or EU per milligram of iron oxide per milliliter.

In one embodiment, the non-pyrogenic preparation is a drug administered to an organism such as an individual or an animal. It preferentially comprises an endotoxin quantity lower than: (i), 5 EU per kilogram of body weight of this organism per hour of administration for non-intrathecal administration and, (ii), 0.2 EU per kilogram of body weight of this organism per hour of administration for intrathecal administration.

In one embodiment, the non-pyrogenic preparation is a medical device, in particular an invasive device. It then preferentially comprises an endotoxin quantity, preferentially measured at the surface of the medical device, which is lower than: (i), 0.5 EU per milliliter of the preparation when the latter is not in contact with the cerebrospinal liquid and, (ii), 0.02 EU per milliliter of the preparation when the preparation is in contact with this liquid.

Preferentially, the non-pyrogenic preparation according to the invention comprises an endotoxin quantity, which abides by the applicable regulatory standards applicable to drug, medical device or cosmetic product, in particular abides by the pharmacopoeia, most preferentially the European and/or American pharmacopoeia(s).

The non-pyrogenic preparation can optionally be administered to an organism within an administration time larger than or equal to the following values: 1, 30 or 60 second(s), 1, 30 or 60 minute(s), 1, 15 or 24 hour(s), 1 or 5 day(s), 1 or 4 week(s). In case where the non-pyrogenic preparation is administered to an organism within an administration time larger than or equal to these values, the quantity of endotoxins comprised in the preparation may be larger than when the same preparation is administered within a time, which is lower than these values.

Preferentially, the quantity of endotoxins in the preparation is measured by a limulus amoebocyte lysate test (LAL). As it will be understood by the person skilled in the art, one will prefer to ensure that the nanoparticles do not interfere with the test, in particular by measuring a recovery rate. This rate can be defined as being equal to $C_{total}/C_1+C_2$, where $C_{total}$ is the endotoxin concentration of suspensions of synthetic nanoparticles mixed with a known quantity of endotoxins of e.g. 0.5 EU/mL. In this example, $C_1$ is the concentration of endotoxins in the different suspensions of synthetic nanoparticles and $C_2$=0.5 EU/mL. It can be considered that there is no interference when this recovery ratio is larger than or equal to 10 or 30, preferentially 50, 100 or 150%.

The pyrogenicity of the preparation according to the invention may be evaluated by a rabbit pyrogenicity test, in particular according to ISO 10993-11, chapter 151 of the American Pharmacopoeia or the European Pharmacopoeia. This test can be carried out by administering the preparation intravenously to 1 or several rabbits, preferentially 3, preferentially using a quantity of synthetic nanoparticles, which is typically but not necessarily larger than or equal to 1 mg. In particular, in the case where the preparation is a medical device, such a quantity appears to be suitable, since it is larger than 6 cm$^2$ per ml or mg of synthetic nanoparticles, in particular recommended by ISO 10993-12 standard. Indeed, considering the surface of cubic synthetic nanoparticle with a side of 50 nm, which is $15.10^{-11}$ cm$^2$, and that 1 mg of synthetic nanoparticle composed predominantly of maghemite comprises $1.6\ 10^{-12}$ synthetic nanoparticles, it can be estimated that 1 mg of synthetic nanoparticles has a surface area of 94 cm$^2$, larger than 6 cm$^2$. The absence of pyrogenicity of the preparation is then demonstrated either by measuring the sum of the temperature increases in three rabbits which must not exceed 10.5, 2 or 1° C., preferentially 2.65° C., in agreement with the European Pharmacopoeia, or by measuring the temperature increase in each rabbit, which should not exceed 10, 5, 2, 1 or 0.1° C., preferentially 0.5° C. in agreement with the American Pharmacopoeia, or by following the recommendations of one or more pharmacopoeias, in particular the European and American pharmacopoeias.

Preferentially, the preparation according to the invention is non-pyrogenic or non-immunogenic. In particular, immunogenicity or pyrogenicity can be caused by non-mineral biological substances, lipids, proteins, enzymes, DNA, or RNA, whether these substances are produced by a different living organism from a humans or are synthesized at least in part by human.

Preferentially, the preparation according to the invention is non-pyrogenic or non-immunogenic when it comprises less than $10^9$, $10^8$, $10^7$, $10^6$, $10^5$, $10^4$, $10^3$, $10^2$, $10^1$, or 1 biological molecule(s), such as protein(s), lipid(s), enzyme(s), DNA, or RNA.

In one embodiment, the preparation according to the invention can be regarded as non-pyrogenic or non-immunogenic when it does not in itself induce a significant response of the immune system, i.e. it does not have a significant pharmaceutical or medical activity; in particular; the preparation does not have any anti-tumor activity in itself. As will be understood by the person skilled in the art, the preparation can have a pharmaceutical or medical activity, such as an antitumor activity when it is exposed to the application of a radiation, such as a magnetic field, preferentially an alternating magnetic field.

In one embodiment, the preparation, the synthetic nanoparticle, its central part and/or its coating can be non-pyrogenic and immunogenic or be non-pyrogenic and non-immunogenic. Pyrogenicity may be considered as an immunogenicity caused by endotoxins.

Preferentially, the synthetic nanoparticles according to the invention have a low level of aggregation, possess a homogeneous distribution in a given medium, preferentially in the preparation and/or in the organism where they are administered. This homogeneous distribution is characterized by: (i), the presence of these synthetic nanoparticles in 0.1, 1, 5, 10, 25 or 50% of this medium, where this percentage can be defined as the volume occupied by the synthetic nanoparticles divided by the total volume of the considered medium, (ii), sedimentation of the synthetic nanoparticles occurring in more than one hour, preferentially in more than one week, most preferentially in more than 15 days, (iii), a sedimentation of the synthetic nanoparticles occurring in a time larger than the administration time of the preparation in an organism. The sedimentation of synthetic nanoparticles can be revealed by the presence of aggregates which sediment, preferentially in a liquid, and which are visible to the naked eye, by optical microscope or by spectroscopic measurements, in particular by absorption.

Preferentially, the synthetic nanoparticles according to the invention are stable in suspension or the preparation according to the invention is stable. Stability is defined as the ability of synthetic nanoparticles to remain in suspension without sedimentation. Stability can in particular be measured by absorption measurements, preferentially by measurements of absorption variation over time at a wavelength where the synthetic nanoparticles absorb, typically between 400 nm and 600 nm, most typically equal to 480 nm, at a wavelength larger than 1, 50, 100, 200, 300, 400, 450, 500, 600 or 800 nm, 1, 5 or 10 μm, at a wavelength lower than 10, 5 or 1 μm, 800, 600, 500, 450, 400, 300, 200, 100, 50 or 1 nm. Preferentially, the stability is such that the optical density or absorption of the suspension of synthetic nanoparticle does not decrease by more than 50, 25, 10, 5, 2, 1 or 0.1%, where this percentage of decrease may be defined as being equal to $[abs(t_0)-abs(t)]/abs(t_0)$, where $abs(t_0)$ and $abs(t)$ are the absorptions measured at the beginning and at the end of the measurement, respectively. In particular, this decrease can be measured over time for a period of more than 1.5, 15, 25, 45 or 60 seconds, 2, 5, 10, 30, 45 or 60 minutes, 2, 5, 10, 50, 100 or 1000 times the time required to administer the suspension of synthetic nanoparticles to an organism. It can be measured just after making the preparation, a few days, a few weeks, a few months, a few years after making the preparation. It is preferentially measured after homogenization of the preparation, in particular by means of sonication, vibration, agitation.

According to one embodiment, the preparation according to the invention is stable for an iron concentration of synthetic nanoparticles larger than 0.01, 0.05, 1, 5, 10, 30, 50, 100, 150, 200, 250, 300, 400, 500, 600, 700, 800 or 900 mg/mL, 1, 2, 5 or 10 g/mL.

In one embodiment, the synthetic nanoparticle has a homogeneity of distribution, a stability, which is(are) larger than that(those) of the synthetic nanoparticles extracted from a living organism, preferentially a magnetotactic bacterium or larger than that(those) of the central part of the synthetic nanoparticles or of SPION or of FION.

In one embodiment, the synthetic nanoparticle may have:
A common property with its central part, preferentially the property ($\alpha$), ($\beta$), ($\chi$), ($\delta$), ($\eta$) (see page 5-6),
A size, which is 0.01, 0.05, 0.1, 0.2, 0.5, 1, 2, 3, 4 5, 6, 7, 8, 9, 10, 15, 20, 50, 75, 100, 250 or 500 nm, 1, 5, 10, 50 or 100 µm larger than the size of its central part and/or coating.
An isoelectric point, in particular an isoelectric point, which is different from that of its central part and/or coating,
A zeta potential, a charge, a surface charge, in particular any of these three parameters and/or variation as a function of pH which is(are) different from that(those) of its central part and/or coating.
A non-pyrogenicity which is lower, larger, or equal to/than that of its central part and/or its coating.

In one embodiment, the coating according to the invention favors the attachment of substances to synthetic nanoparticles, enables to limit the toxicity and results in a specific organization such as: (i), a chain arrangement, i.e. an arrangement of at least two synthetic nanoparticles linked together with a possible alignment of crystallographic axes or field lines of these nanoparticles, (ii), an arrangement within a geometric figure, (iii), ordered and characterized by the presence of a geometric pattern, such as a circle, a rectangle, a diamond, a square, an eclipse. Such an organization can be highlighted by TEM measurements, in particular by depositing a drop of the preparation of synthetic nanoparticles at a suitable concentration to be able to observe the arrangements of the synthetic nanoparticles in their assemblies.

In one embodiment, the coating does not originate from the organism which synthesizes the central part of the synthetic nanoparticles, which may facilitate its characterization, in particular when the structure or composition of the coating is known, simple, identifiable or easily characterizable.

In one embodiment, the coating is a non-pyrogenic substance.

In one embodiment, the coating comprises at least one compound, which is able to establish weak interactions or covalent bonds with the central part of the synthetic nanoparticles, in particular iron oxide.

In one embodiment, the coating comprises at least one compound able to be chemisorbed or physisorbed on the central part of the synthetic nanoparticle.

In one embodiment, the coating comprises at least one compound able to establish interactions or bonds with $Fe^{2+}$ or $Fe^{3+}$ ions, hydroxyls $OH^-$, oxides $O^{2-}$, crystalline defects of the central part, which may be in or at the surface of the central part of synthetic nanoparticles.

In one embodiment, the coating comprises at least one compound, atom, ion, or chemical function such as an acid, carboxylic acid, phosphoric acid, or sulfonic acid function, wherein the compound, atom or ion comprised in the coating is able to establish interactions or bonds with the central part or with at least one atom of the central part, a chemical function of the central part, an ion of the central part such as $Fe^{2+}$, $Fe^{3+}$, Hydroxyl $OH^-$, oxide $O^{2-}$ or a crystalline defect of the central part.

The atom, the chemical function or the ion of the central part may be in or at the surface of the central part of the synthetic nanoparticles.

In one embodiment, the coating is chosen from the compounds which yield better heating properties for the synthetic nanoparticles than for SPION or FION. It is thus preferred that the coating comprises substances, which are good thermal conductors.

In one embodiment, the coating is chosen from compounds which produce among synthetic nanoparticles an organization or assembly properties, which favor the effects of a radiation or of a magnetic field such as an alternating magnetic field on these synthetic nanoparticles. The effects of a radiation or of a magnetic field may in particular be movements, vibrations, rotations, or translations of these nanoparticles.

In one embodiment, the coating has a thickness which is less than the average diameter of the central part of the synthetic nanoparticles, less than half, a quarter of that diameter, less than 10.5, 2.5 or 1 µm, 500, 400, 300, 200, 100, 90, 80, 70, 60, 50, 40, 30, 20, 10, 5, 4, 3, 2, 1 or 0.5 nm. Such a thickness may in particular enable to limit the toxicity.

In one embodiment, the coating has a thickness typically larger than the average diameter of the central part of the synthetic nanoparticles, larger than one-half, one-fourth of this diameter, larger than 0.1, 0.5, 1, 2, 4, 8, 10, 15, 20 or 25 nm. Such a thickness may in particular enable to link the synthetic nanoparticles together or prevent the formation of aggregates. Advantageously, the presence of a sufficiently thick coating enables to prevent the synthetic nanoparticles from sticking together, in particular under the effect of the magnetic forces which they exert on each other and whose intensity is the highest when these synthetic nanoparticles become the closest to each other.

In one embodiment, the percentage of variation of the thickness of the coating is defined as being the smallest divided by the largest thickness of the coating that can be measured on the synthetic nanoparticle(s) in the preparation, using in particular TEM. In a first case, the thickness of the coating is homogeneous. The percentage of variation in thickness is then preferentially lower than $10^6$, $10^5$, $10^4$, $10^3$, 500, 100, 50, 10, 5, 1 or 0.1%. A homogeneous thickness can in particular allow a homogeneous distribution of the synthetic nanoparticles. In a second case, the thickness of the coating is inhomogeneous. The percentage of variation in thickness is then larger than 0.1, 1, 5, 10, 50, 100, 500, $10^3$, $10^4$, $10^5$ or $10^6$%. An inhomogeneous thickness can in particular result in a distribution of magnetic forces of various strengths.

In one embodiment, the coating has an iron content lower than or equal to 1, 2, 5, 10, $10^2$, $10^3$, $10^4$, $10^5$ or $10^6$ times that of the central part of the synthetic nanoparticles.

In another embodiment, the coating possesses a content in at least one other atom than iron and oxygen which is larger than or equal to 1, 2, 5, 10, $10^2$, $10^3$, $10^4$, $10^5$ or $10^6$ times that of the central part of synthetic nanoparticles.

In one embodiment, the coating is a surfactant inducing a variation in surface tension at the surface of the synthetic nanoparticles, larger than $10^{-4}$, $10^{-3}$, $10^{-2}$, $10^{-1}$, 1, 5, 10, 20, 50 or 100% where this percentage is defined as equal to TS(CP)−TS(SN)/TS(CP), where TS(CP) and TS(SN) are surface tensions of the central parts and synthetic nanoparticles, respectively.

In one embodiment, the coating comprises carbonaceous compounds.

In one embodiment, the coating comprises at least one compound selected from the group consisting of a chelator, an amphiphatic molecule, a polarized or charged polymer, a metal or silicon oxide, a metal or silicon hydroxide, an acid, an acidic, basic, oxidized, reduced, neutral, positively charged, negatively charged, derivative of these compounds, and a combination of several of these compounds or derivatives.

In one embodiment, the coating comprises at least one compound selected from the group consisting of a polysaccharide, a fatty acid, a phospholipid, a polymer of amino acids, polymeric or non-polymeric silica, and an aliphatic amine polymer, of an acidic, basic, oxidized, reduced, neutral, positively charged, negatively charged derivative of these compounds, and a combination of several of these compounds or derivatives.

In one embodiment, the coating does not comprise phospholipids or proteins or RNA or DNA or compounds of bacterial, cellular or biological origin or compound derived from a magnetotactic bacterium.

In one embodiment, the coating comprises at least one function selected from the group consisting of phosphoric acids, carboxylic acids, sulfonic acids, esters, amides, ketones, alcohols, phenols, thiols, amines, ethers, sulfides, acid anhydrides, acyl halides, amidines, nitriles, hydroperoxides, imines, aldehydes, peroxides, of an acidic, basic, oxidized, reduced, neutral, positively charged, negatively charged derivative of these compounds, and a combination of several of these compounds or their derivatives.

In one embodiment, the coating according to the invention is chosen from sterilizable substances, preferentially by autoclaving, biocompatible, biodegradable substances, which do not induce metabolic, immunological, cytotoxic, pharmacological effect, which can be administered by an intravenous and/or immunological route. Such a substance can be povidone, PEG 400, poloxamer 188, dextran, phosphatidylcholine, dipalmitoyl-sn-glycero-3-phosphatidylcholine, or a derivative of these substances.

The type of coating can be selected according to the following parameters:
(i) Administration route of synthetic nanoparticles: for example, for an intravenous administration, a coating that enables to prevent macrophages from capturing synthetic nanoparticles, such as PEG or dextran can eventually be chosen,
(ii) Cellular internalization: to support it, a coating with a positive charge such as poly-L-lysine can "eventually" be chosen.

In one embodiment, the preparation according to the invention can be used as drug or as diagnostic agent, in particular in the context of the treatment of a tumor, for example using magnetic hyperthermia.

In one embodiment, a medical, veterinary or cosmetic intervention or operation using this preparation involves at least one of the following sequences, preferentially in the indicated chronological order:
(i) administration of the preparation to an organism, in particular by a local route, muco-cutaneous, enteral, parenteral, intra-tumoral, intravenous or intra-arterial,
(ii) targeting of synthetic nanoparticles towards part of an organism, such as an organ, a tumor, a blood vessel,
(iii) treatment or detection of that part of the organism.

In one embodiment, the preparation according to the invention can be used for cosmetic applications.

In one embodiment, the preparation according to the invention is administered at a concentration, which is larger than the maximum concentration at which a suspension comprising chains of magnetosome extracted from magnetotactic bacteria can be administered, preferentially 14 mg/mL in iron. It may also be administered at an iron concentration, which is larger than or equal to 0.01, 0.05, 1, 5, 10 or 15 mg/mL, preferentially 25, 50, 100 or 150 mg/mL, most preferentially larger than or equal to 200, 300, 400, 500, 600, 700, 800 or 900 mg/mL, 1, 2, 5 or 10 g/mL. This may be enabled by the larger solubility or the lower sedimentation of the synthetic nanoparticles compared to that of the chains of magnetosomes extracted from magnetotactic bacteria and/or that of SPION and/or that of FION.

In one embodiment, the preparation according to the invention can be administered at an iron concentration lower than or equal to 1 kg/mL, 500, 250, 100, 50, 10, 5, 2 or 1 g/mL, preferentially lower than or equal to 900, 700, 500 or 400 mg/mL, most preferentially lower than or equal to 300, 200, 150, 100, 10, 1 or 0.1 mg/mL.

In one embodiment, the treatment can be carried out by applying an alternating magnetic field, a technique commonly referred to as magnetic hyperthermia, whereas the detection can in particular be carried out by magnetic resonance imaging (MRI).

In one embodiment, the invention relates to a pharmaceutical composition or drug comprising, as active principle, a preparation as described above and optionally at least one pharmaceutically acceptable carrier.

In one embodiment, the invention relates to a medical device comprising the preparation according to the invention.

In an embodiment, the invention relates to a diagnostic composition comprising the preparation according to the invention.

In one embodiment, the invention relates to a cosmetic composition comprising, as cosmetic active principle, the preparation according to the invention.

In one embodiment, the invention relates to a method for treating a tumor in an individual or animal wherein one administers a therapeutically active quantity of the preparation according to the invention.

In one embodiment, the invention relates to a method for the manufacture of a preparation as described above, comprising the following sequences:
(i), from a preparation of nanoparticles synthesized by a living organism comprising a crystallized mineral central part composed predominantly of iron oxide and a biological surrounding coating, isolate the mineral central part;
(ii), treat the resulting preparation to cover the central part with a surrounding coating;
(iii), optionally sterilize the preparation, preferentially after sequence (i), possibly after sequence (ii).

In one embodiment, the central part of the magnetosomes is surrounded or not by compound(s) or substance(s) not belonging to this central part.

In one embodiment, treated magnetosomes are associated with magnetosomes, which have undergone a treatment, in particular following the sequence of bacterial fermentation.

In one embodiment, the sequences (i) and/or (ii) can involve:
(a), a chemical purification process, called the said chemical purification process, whose objective is in particular to remove, by a chemical method, all or part of the material surrounding the central parts of the magnetosomes. It can consist in mixing any suspension of the sequences (i) or (ii) with a chemical solution, designated the said chemical solution, preferentially at a concentration larger than 0.001, 0.01, 0.1, 1, 10 or 100 μM, 1, 10 or 100 mM, 1 M, preferentially at a concentration lower than 1000, 100, 50, 10, 5, 2 or 1 M, 500, 100, 50, 10, 5 or 1 mM, 100, 50, 10, 5, or 1 μM. This chemical solution may be a hypo-osmotic solution, a lysis buffer, a solution for desorbing or detaching the magnetosomes from certain surfaces, for removing all material, in particular organic, not located in or at the surface of the magnetosome central part, for removing some residues of detergents. This chemical solution can comprise the following chemical substances: (i) chemical denaturants such as sodium hydroxide, potassium hydroxide or solution with neutral, acidic or basic pH, (ii), organic solvents such as toluene, ether, alcohol, phenylethyl, dimethyl sulfoxide (DMSO), benzene, methanol, chloroform, (iii), chaotropic agents such as urea, phenol, guanidine, guanidium chloride, guandinium thiocyanate, which are in particular able to bring hydrophobic compounds into aqueous solutions by modifying the structure of water, (iv), chelating agents such as ethylene diamine tetraacetic acid (EDTA), (v), substances used in depyrogenation such as sodium hydroxide, urea, hydrogen peroxide, enabling to remove or neutralize endotoxins, (vi), antibiotics, such as thionines, (vii), surfactants such as triton, Brij, Duponal, (viii), reducing agents such as dithiothreitol (DTT), thioglycolate, β mercaptoethanol, which can in particular enable to break bonds or disulfide bridges, (ix), detergents, compounds with a hydrophobic hydrocarbon group and a hydrophilic charged extremity, (x), surfactants. Among the detergents which can be used are ionic, cationic, or anionic detergents, nonionic detergents, zwitterionic detergents, chaotropes, sodium dodecyl sulphate (SDS), desoxycholate, cholate, triton, in particular triton X100, n-Dodecyl1β-D-maltoside (DDM), digitonin, tween 20, tween 80, 3-[(3-cholamidopropyl)dimethyl-amino]-1-propanesulfonate (CHAPS), urea, guanidine hydrochloride, nonyl phenoxypolyethoxylethanol (NP-40). The said chemical solution can also comprise water or any of the derivative(s) of the previously mentioned chemical substance(s);

(b), a biological purification process, called the said biological purification process, whose objective is in particular to remove by a biological process all or part of the material surrounding the central part of the magnetosomes. It can in particular involve a living organism or a substance derived from such an organism, such as an enzyme, in particular a lytic enzyme, a phage, a protein such as protease or mannase;

(c), a chemical coating process, called the chemical coating process, consisting in mixing the suspension comprising the central parts of the magnetosomes with any substance or combination of substances used for coating the central part of the magnetosomes, wherein the said substance(s) is(are) called the said coating substance(s);

(d), a thermal process, called the said thermal process, consisting in exposing any suspension obtained during sequences (i) or (ii) to a temperature gradient, in particular larger than or equal to 10, 25, 50, 100, 150, 200, 300, 500, 1000, 2000, 3000 or 5000° C. and/or in bringing any suspension obtained during sequences (i) and/or (ii) at a temperature, which is preferentially lower than or equal to 100, 50, 10, 0, −10, −40, −70, −77, −150, −250° C., 50, 30, 10 or 1 K, which is preferably larger than or equal to 1, 5, 25, −250, −70, −77, −50, −20, 0, 5, 20, 40, 100, 200, 500, 1000, 2000, 4000 or 5000° C.

(e), a mechanical process, called the said mechanical process, consisting in applying to any of the suspensions obtained during sequences (i) and/or (ii): (1), a pressure, preferentially larger than 1, 10, 100, 500, $10^3$, $10^4$, $10^5$, $10^6$, $10^7$, $10^8$ or $10^9$ atmosphere(s), preferentially lower than $10^9$, $10^8$, $10^7$, $10^6$, $10^5$, $10^4$, $10^3$, 500, 100, 10 or 1 atmosphere(s), in particular by using an instrument such as a high pressure homogenizer, a French press, a disrupting bomb or a ball mill, (2), sonication, in particular at a power larger than 0.01, 0.1, 0.5, 1, 2, 5, 7, 10, 20, 40, 100, 500 or 1000 Watt, at a power lower than 1000, 500, 100, 40, 20, 10, 7, 5, 2, 1, 0.5, 0.1 or 0.01 Watt, wherein the length of time of sonication is preferentially larger than 1, 2, 5, 10, 20, 30, 45 or 60 second(s), larger than 2, 5, 10, 20, 30, 45, 60 or 120 minutes, larger than 2, 3, 4 or 5 hours, preferentially less than 60, 30, 15, 5 or 1 minute(s), less than 60, 45, 30, 15, 10 or 1 second(s), (3), irradiation, in particular using ionizing rays;

(f), a process of magnetic selection, called the said magnetic selection process, consisting in isolating the central part of the magnetosomes or the treated magnetosomes from substances with no or low magnetism, defined as being bacterial debris, un-lysed bacteria, dissolved iron, dissolved magnetosomes or any material comprised in any suspension of sequences (i) or (ii), which comprises no or a low quantity of magnetosomes, preferentially less than $10^9$, $10^8$, $10^7$, $10^6$, $10^5$, $10^4$, $10^3$, $10^2$ or 10 magnetosomes per milliliter of preparation. For this purpose, a magnetic field gradient may be applied to any suspension of the sequence (i) or (ii), where such a suspension is preferentially comprised in a container such as a tube or a bottle, preferentially composed of glass or of a material that does not adsorb the modified magnetosomes or the central parts of the magnetosomes. This magnetic field gradient enables in particular the migration of the magnetic substances, preferentially the central parts of the magnetosomes or the modified magnetosomes, towards the area where the magnetic field is the most intense such as the wall of the container, to concentrate them in this area and thus to isolate them. This magnetic field gradient is preferentially of larger intensity than the earth's magnetic field strength, at 0.1, 1, 10 or 100 µT, 0.1, 1, 10 or 100 mT, 0.1, 1, 10, 50 or 100 T. It is in particular of sufficient intensity to enable magnetic substances, such as the central parts of magnetosomes or modified magnetosomes, to be separated from substances with no or low magnetism. This magnetic field gradient is preferentially of lower strength than 100 or 50 T, most preferentially at 5 or 1 T, 100, 50, 10 or 1 mT. In particular, it may be of sufficiently low strength to avoid attracting substances with no or low magnetism. Such magnetic field gradient can be applied by a magnet, such as a Neodymium magnet, an electromagnet or any instrument or material able to generate a magnetic field whose intensity varies preferentially spatially and/or temporally. The magnetic field gradient may be applied for more than 1.5, 10, 30, 45 or 60 second(s), 5, 10, 30, 45 or 60 minutes, 2, 5, 10, 15 or 20 hours, 1, 2 or 5 day(s), 1, 2, 3 or 4 week(s), 2, 4 or 6 months. Following application of the magnetic field gradient, the supernatant of the suspension, which does not comprise or comprises in small quantity the central parts of the magnetosomes or the modified magnetosomes, can be removed and replaced by a substance such as a solvent, preferentially non-pyrogenic, such as non-pyrogenic water;

(g), another selection process, called the said other selection process, during which the central parts of the magnetosomes or the modified magnetosomes can be isolated from the bacterial debris, in particular by using a tangential filtration system possessing columns with pores whose sizes either enable bacterial debris to pass through, but not the central parts of the magnetosomes, or enable the central parts of the magnetosomes to pass through, but not to the bacterial debris. This size is notably lower than 100, 50, 20, 10, 5, 1, 0.5, 0.2, 0.1, 0.05, 0.02, 0.01, 0.005 or 0.0001 µM. This size may preferentially be between 0.02 µm and 2 µm, preferentially between 0.2 µm and 1 µm, most preferentially between 0.2 µm and 0.4 µm; In one embodiment, sequence (i) is preceded by a sequence of culture of a living organism, such as a magnetotactic bacterium, which synthesizes magnetosomes.

In one embodiment, the culture sequence of the living organism is carried out under conditions that are not fully controlled, such as the culture conditions of magnetotactic AMB-1 bacteria in bottle.

In another embodiment, the sequence of culture of the living organism is carried out under controlled conditions such as the culture conditions of MSR-1 magnetotactic bacteria in fermenter, which involve: (a) an acidic nutritive solution comprising iron to keep the pH of the growth medium constant during the growth of the bacteria and, (b), air supply during the growth of bacteria to promote this growth while keeping the oxygen concentration of the culture medium at a low value, preferentially lower than 20 mbar, most preferentially lower than 2 mbar, in order to enable magnetosome synthesis.

In one embodiment, the sequence (i) is subdivided into three sequences that preferentially but not necessarily follow each other in the indicated order: (i1), lysis of magnetotactic bacteria, (i2), removal of the material, in particular organic, which is not part of the central part of the magnetosomes and which could not be removed during i1, (i3), recovery and washing of the suspension comprising the central parts of the magnetosomes. All of these sequences can be carried out using any combination of the said processes (a) through (g), repeated one or several times.

In one embodiment, the sequence (i1) can begin with the concentration of the magnetotactic bacteria, in particular by centrifuging at 1000-10000 g and/or by using the said other selection process, preferentially using a tangential filtration system, where the size of the holes is lower than the size of the magnetotactic bacteria. The concentration of bacteria at the end of this sequence may be between 1.1 and $10^4$ times larger than the bacterial concentration measured at the beginning of (i1). Then, the magnetotactic bacteria, concentrated or not, can be lysed. Lysis can be carried out by osmotic shock, using the said chemical process in which the said chemical solution is preferentially a lysis buffer. It can be carried out by adding a larger volume of lysis buffer than the volume of bacteria, preferentially equal to 2 to 100 times the volume of bacterial lysate, most preferentially equal to 4 times the volume of bacteria. At the end of this sequence, one obtains a suspension of treated magnetosomes, extracted from the bacteria, mixed with bacterial debris and possibly with a certain quantity of non-lysed magnetotactic bacteria.

In another embodiment, the sequence (i2) consists in treating the magnetosome suspensions obtained at the end of (i1) to remove the remaining material, in particular organic material, preferentially using the said chemical solution, preferentially using detergents, such as phenol or dichloromethane, making it possible to remove the membrane or the material, in particular organic, surrounding the treated magnetosomes.

In another embodiment, sequence (i3) consists in washing the suspension obtained in (i2) several times to remove all the residues coming from the detergent and to obtain a suspension comprising the central parts of the magnetosomes.

In one embodiment, the sequence (ii) consists in covering the central part of the magnetosomes with a coating, preferentially non-pyrogenic. It may be carried out using the said chemical coating process, in particular by mixing the suspension comprising the central parts of the magnetosomes obtained at the end of (i3) with a suspension comprising the coating. This mixture can be carried out by homogenization, by sonication, preferentially low-power sonication, of less than 500, 250, 100, 50, 25, 10, 5, 2 or 1 Watt, in particular using a sonicating finger or a sonicating bath, by stirring, by heating, by radiation and thus allowing the coating to adhere to or associate with the surface of the central parts of the magnetosomes. The mixture can be carried out at neutral, acidic or basic pH, preferentially at a pH enabling to promote the chemical interactions and/or chemical reactions resulting in an association between the coating and the central parts of the magnetosomes. The mass of the coating used is preferentially between one thousandth and one thousand times the mass of the central parts of the magnetosomes, preferentially between one hundredth and one hundred times this mass, most preferentially between one tenth and ten times this mass. At the end of the sequence (ii) a suspension is obtained comprising the central parts of the magnetosomes covered with a non-pyrogenic coating.

In one embodiment, the central part of the magnetosomes obtained at the end of the sequence (i3) is sterilized, preferentially using a method which does not denature this central part, such as autoclaving. The sequence (ii) is then preferentially carried out in a sterile environment in order to obtain a non-pyrogenic preparation at the end of the sequence (ii).

In one embodiment, the suspension obtained at the end of sequence (ii) is sterilized, preferentially using a method such as gamma rays which does not destroy the coating and the central part of the magnetosomes.

In one embodiment, the yield obtained from the suspension comprising the coated central parts of the magnetosomes is estimated as being equal to the quantity of iron comprised in this suspension divided by the quantity of initial iron comprised in the suspension of magnetotactic bacteria before the lysis sequence. This yield is preferentially larger than 1, 2, 5, 10, 25, 50, 75 or 100%. This yield can be optimized by combining several of the said processes with one another and/or by repeating one or more of the said process(es).

EXPERIMENTAL EXAMPLES

Description of the Tables:
Tables 1 and 2:

Properties of various types of suspensions comprising BNF-Starch, whole bacteria, central parts of uncoated magnetosomes, central parts of magnetosomes coated with poly-L-lysine, chitosan, carboxy-methyl-dextran, citric acid, oleic acid, silica, folic acid, DOPC, alendronate, neridronate, PEI, $Al(OH)_3$, where the species of magnetotactic bacteria are AMB-1 and MSR-1. In table 1: Endotoxin concentration measured in EU per milligram of iron per milliliter of suspension, percentage of decrease after 20 minutes of absorption, measured at 480 nm, of 1 mg of the various suspensions, variation in temperature ($\Delta T$) and initial slope of this variation ($\delta T/\delta t$) for the suspensions brought into contact with GL-261 cells treated according to condition 3, percentage of living cells for the suspensions brought into contact with GL-261 cells treated according to conditions 1, without field (−B), and according to condition 2, with field with a maximum temperature increase of 45° C.,% living cells (+B). The percentage of living cells is the number of living cells treated under conditions 1 or 2 divided by the number of untreated living cell number at 37° C. For the first study with BNF-Starch, the percentage of living cells is the number of living cells treated under conditions 1 or 2 divided by the number of untreated living cells at 45° C. In table 2: Coating thickness in nm, isoelectric point in pH unit, hydrodynamic size in nm, zeta potential measured in mV as a function of pH, of coated or uncoated synthetic nanoparticles, comprised in the various suspensions, percentage of nitrogen (% N), carbon (% C), hydrogen (% H), sulfur (% S) in coated or uncoated synthetic nanoparticles.

Table 3:

Binding properties of the central parts between each other for different coatings.

Material and Methods:

Determination of the Concentration in Iron of the Different Nanoparticle Suspensions:

The nanoparticles are first dissolved by 12N hydrochloric acid and $Fe^{2+}$ ions are oxidized to $Fe^{3+}$ ions with hydrogen peroxide. Potassium thiocyanate is then used to complex the $Fe^{3+}$ ions and $Fe^{3+}$ concentration is determined by measuring the absorption of the complex at 476 nm.

Transmission Electron Microscopy (TEM):

TEM is used to determine the size, distribution in size of the different nanoparticles, nanoparticle coating thickness and the type of nanoparticle organization. To carry out TEM studies, the different suspensions are washed twice and re-suspended in MilliQ autoclaved water to obtain a concentration in iron of 300 μg/ml. 5 μl of each suspension are deposited on top of carbon grid. Grids are dried during at least two hours at room temperature and then observed under TEM (JEOL LaB6 JEM-2100).

Test of Limb Amoebae Lysate (LAL):

LAL tests are carried out under sterile conditions using Thermo Scientific kit 88282 called "Pierce LAL Chromogenic Endotoxin Quantitation Kit". 1 ml of each suspension, homogenized by sonication and washed with non-pyrogenic water, is first heated at 70° C. for 10 minutes in a dry bath to denature any residual proteins which could distort the results of the LAL test. 25 μl of each suspension comprising 10 μg of iron are then introduced into the wells of a microplate maintained at a temperature of 37° C. throughout the duration of the experiment. 25 μl of the LAL kit solution are added to initiate the reaction. After 10 minutes of reaction, 50 μl of the chromogenic substrate are introduced into the wells for 6 minutes to enable detection of the quantity of endotoxins. Finally, 25 μl of acetic acid are added to stop the reaction. The optical density of the obtained suspensions is measured at 405 nm using a microplate reader. The concentration of endotoxins is then estimated using a standard range supplied with the kit. In order to verify that the LAL test does not interfere with the nanoparticles, a recovery rate, defined as being equal to $C_{total}/C_1+C_2$, is measured, where $C_{total}$ is the endotoxin concentration of the nanoparticle suspensions mixed with a known quantity of Endotoxins of 0.5 EU/mL, $C_1$ is the concentration of endotoxins in the different nanoparticle suspensions and $C_2$=0.5 EU/mL. The recovery rate estimated during the different measurements is larger than 50%, indicating that the nanoparticles do not interfere with the LAL test.

Elementary Analyzer of Carbon, Hydrogen, Nitrogen and Sulfur (CHNS):

Measurements are carried out using a CHNS analyzer (Flash EA 1112 Analyzer from Thermo Fischer scientific) using 10 mg of iron of each lyophilized suspension, enabling to determine the percentage in carbon, nitrogen, hydrogen and sulfur of these suspensions.

Scattering Measurements:

The zeta potential and the hydrodynamic size (hydrodynamic diameter in the case of spherical objects) of the various nanoparticles are measured using the Malvern Instruments Zetasizer Nano ZS. The spherical objects are identified with the decreasing exponential profile of the correlation function. For the measurements, the suspensions of nanoparticles comprise 30 μg/ml of iron and are at a pH adjusted between 2 and 12 using solutions of hydrochloric acid and sodium hydroxide.

Absorption Measurements:

The variation over time of the absorbance of the different nanoparticle suspensions is measured at 480 nm using a UviLine9400 Secomam absorption spectrophotometer.

Determination of the Primary Amine Concentration for 1 mg in Iron of the Suspension of Central Parts of the Synthetic Nanoparticle:

A method for controlling the purity of the central part is the dosage of amines via TNBSA (2,4,6-trinitrobenzene acid Sulfonic acid), which has the particularity of reacting with primary amines. The first step is to add 1 mg of iron of the central part to a 0.1 M sodium bicarbonate buffer solution at pH 8.5 and then TNBSA (R'—SO3H) is added, which leads to the following reaction: $R-NH_2+R'-SO_3H \Longleftrightarrow H_2SO_3+R'-NH-R$. This reaction is carried out at 37° C. for 2 h and the obtained compound being colored in yellow (R'—NH—R), its amine concentration is determined by absorption at 405 nm. This concentration is equivalent to that of the central part. A calibration curve is carried out with glycine which has a primary amine function.

Determination of the Phosphate Concentration for 1 mg in Iron of Suspension of Central Part of the Synthetic Nanoparticle:

The assay of the phosphate groups of the central part is carried out by colorimetry Ammonium molybdate (($NH_4)_2MoO_4$) first reacts in the presence of phosphate (coming from a stock solution (DOPC) for calibration or coming from samples to be assayed after digestion with perchloric acid at 70% for 2 h at 130° C.). The precipitate of Molybdate is yellow and unstable. Very rapidly, ascorbic acid is added which will reduce this complex to give a blue colored molybdate salt, which is a stable compound (one heats for 5 minutes at 100° C. in a dry bath to activate this reduction) and one measures the quantity of complexed phosphate by absorbance at 800 nm.

Cellular Toxicity and Temperature Measurement of the Various Nanoparticles Exposed or not to the Application of an Alternating Magnetic Field:

The GL261 cells are seeded in a T175 flask until reaching 70-80% confluence, the supernatant is removed, 4 ml of Trypsin-EDTA at 0.25% are added to the cells, the cells are incubated for 5 minutes and then detached. Trypsin is deactivated by adding 30 ml of cell medium. The cells are then diluted to a concentration of $1.25 \cdot 10^6$ cells per milliliter after centrifugation at 700 rpm for 10 minutes at 4° C. 400 μl of cells are introduced into Eppendorf tubes in order to reach $\sim 5.10^{+5}$ cells per condition. The various suspensions of synthetic nanoparticles were added to the tubes at a final concentration of 1 mg/ml in iron. The eppendorf tubes are then heated for 10 minutes at 37° C. 3 conditions follow. For treatment condition 1, the tubes are maintained at 37° C. for 30 minutes using a dry heating bath. For treatment condition 2, the tubes are maintained at 45° C. for 30 minutes by applying an alternating magnetic field of frequency 198 kHz and average strength adjusted between 23 and 46 mT to maintain the temperature at 45° C. For the treatment condition 3, the tubes are exposed to the application of an alternating magnetic field of frequency 198 kHz and average strength of 32 mT for 30 minutes. Temperature variations over time are measured using a thermocouple probe placed in the eppendorf tubes. After the treatments, the contents of the tubes are introduced into a flask T 25 to which is added 6 ml of RPMI medium and 10% of fetal calf serum. The cells are incubated for 24 hours in the presence of 5% $CO_2$. 24 hours later, a cell viability test is carried out with Trypan blue, enabling to discriminate the colorless living cells from the colored dead cells.

Example 1: Characterization of Suspensions Comprising BNF-Starch

Nanoparticles synthesized chemically by the company Micromod, called BNF-Starch (Reference: 10-00-102), are tested. These iron oxide nanoparticles are surrounded by hydroxyethyl starch and have a hydrodynamic diameter of 119 nm. They have an isoelectric point of pH 9.5, a zeta potential which varies from 7 mV at pH 2 to −20 mV at pH 12 and a percentage of carbon measured with the CHNS of 8.7%. The TEM measurements enable to estimate the thickness of the coating, from 1 to 4 nm. The variation in absorption with time, measured at 480 nm, of a suspension comprising 1 mg of BNF-Starch does not decrease in 20 minutes, indicating the stability of this suspension. An LAL test, performed on these suspensions, revealed a low level of endotoxins (<50 EU/mg/ml). For a first series of measurements, table 1 shows that when a mixture of a suspension of BNF-Starch and GL-261 cells is subjected to condition 3 of the treatment, the temperature of the mixture slightly increases by 6.2° C. from 36.5° C. before application of the field to 42.7° C. after 30 minutes of application of the field. The initial slope of the temperature variation is estimated to be 0.009° C./sec. When this same mixture is subjected to the treatment condition 2, table 1 shows that the percentage of living cells is 78±5%, similar to that of 71±5% obtained in treatment condition 1, without field. This indicates the low cytotoxicity induced by BNF-Starch on GL261 cells in the presence of treatment condition 2 by comparison with cells heated to 45° C. In a second series of measurements, when the mixture is subjected to treatment condition 2, table 1 shows that the percentage of living cells is 31%, lower than 86% obtained during treatment condition 1, without field when this percentage is estimated by comparison with the number of living cells at 37° C. This indicates the cytotoxicity induced by BNF-Starch on GL261 cells in the presence of treatment according to condition 2 compared to cells heated to 37° C.

Example 2: Pyrogenic Chains of Magnetosomes Extracted from the Strain AMB-1

Preparation:

*Magnetospirillum* AMB-1 bacteria (ATCC, strain 79024) are first introduced into sterile culture medium comprising the nutrients and additives necessary for the proliferation of magnetotactic bacteria and the production of magnetosomes (medium ATCC 1653) and the media are then placed in an incubator at 30° C. for 7 days. After 7 days, the media are centrifugated, the bacterial pellet is washed, the magnetotactic bacteria are concentrated by using a magnet, introduced into a tube comprising 1 mL of TRIS 0.05 M, sonicated using a Sonicating finger for 2 hours at 30° C. at 0° C. and then washed 17 times with sterile Millipore® water using a magnet. A suspension comprising pyrogenic magnetosome chains extracted from the magnetotactic bacteria is obtained.

Characterization:

TEM measurements showed the presence in these suspensions of magnetosome chains with lengths between 50 and 800 nm, magnetosome sizes between 5 nm and 60 nm. The thickness of the coating is 1 to 5 nm. The absorption of these suspensions comprising 1 mg of iron, measured at 480 nm, decreases by 30% after 20 minutes, which shows the low sedimentation of these suspensions. Light scattering measurements on these chains indicate the presence of three chain populations, 5% with a hydrodynamic size (HS) 176 nm, 81% with HS 986 nm, and 14% with HS 4363 nm. They have an isoelectric point of pH 4.2, a zeta potential which varies from 20 mV at pH 2 to −38 mV at pH 12. The CHNS analysis reveals a percentage of carbon in these chains of 13.9%. The endotoxin concentration of these suspensions, measured by the LAL test, was estimated at a high value of between 18,000 and 150,000 EU per ml per mg of iron oxide. The presence of endotoxins was also suggested by Fourier transform infrared absorption measurements using a Nicolet FT-IR model 380 spectrometer. These spectra indicate the presence of peaks at 1250 $cm^{-1}$ and 1050 $cm^{-1}$, which can be attributed to the vibrations of phosphate groups of lipopolysaccharides and phospholipids. In a first series of measurements, when the pyrogenic magnetosome chains extracted from AMB-1 are mixed with GL-261 cells and the mixture is subjected to treatment condition 3, the temperature of the mixture increases from 20.5° C., from 36° C. before application of the field to 56.5° C. after 30 minutes of application of the field. The initial slope of the temperature variation is estimated at 0.043° C./sec. This increase in temperature is larger than that observed for BNF-Starch. In a second series of measurements, when this mixture is subjected to the treatment condition 2 in the presence of the field, table 1 shows that the percentage of living cells is low at 10% and lower than 55% obtained during the condition 1 of treatment, without field. This indicates the cytotoxicity induced by these pyrogenic magnetosomes on GL261 cells in the presence of treatment under conditions 1 and 2 with a larger cytotoxicity for condition 2 (in the presence of the field) than for condition 1 (absence of the field).

Anti-Tumor Efficacy on U87-Luc Tumors Implanted in Mouse Brain:

Efficacy experiments were carried out on 7 groups of ten mice in which U87-Luc intracerebral tumors were grown with volumes between 1 and 29 $mm^3$. During these experiments, the mice are fed according to the procedures in force and watered at will. The general condition of the animals is monitored daily, the mice are weighed every two days and are euthanized when a reduction in their body weight larger than 15%, signs of pain, an unusual posture, are observed. The 7 different groups of mice received 8 days after the injection of the U87-Luc cells at the injection site of the tumor cells (2.2.0): a solution of 2 μL of 0.9% NaCl (groups 1 and 2); 2 μL of a suspension of magnetosomes at 20 mg/mL in maghemite (groups 3, 4 and 5); 2 μL of a suspension of BNF-Starch at 20 mg/mL in maghemite (groups 6 and 7). 8 days after injection of U87-Luc cells, the mean tumor volumes for groups 1, 2, 3, 4, 5, 6 and 7 are 29, 10, 5, 3, 25, 10 and 2 $mm^3$, respectively. Groups of mice 2, 4, 5 and 7 are exposed 3 times per week for 5 weeks to an alternating magnetic field of average strength 25 mT and frequency 198 kHz for 30 minutes. Histological studies are carried out on the mice of group 4 to determine whether the tumor completely disappears 150 days after the administration of the magnetosome chains. The tissues studied in histology are taken from euthanized mice, the brains are extracted, fixed with a 4% paraformaldehyde solution, cut into transverse slices 2 mm thick, included in 3 μm thick paraffin blocks, collected on glass slides and then stained with hematoxylin-eosin (H & E) to distinguish the healthy area from the tumor area. Finally, the temperature is measured during the different treatments using an infrared camera.

In mice comprising only tumors, treated by the administration of nanoparticles alone (magnetosome chain and BNF) or by the multiple applications of the alternating magnetic field, the tumor volumes increase rapidly to reach an average volume of 150 mm$^3$ in less than 40 days following administration of the tumor cells. Mean survival times of mice belonging to groups 1, 2 and 6 were estimated as 38 days on average. These results suggest that neither the application of the alternating magnetic field nor the sole administration of BNF-Starch or magnetosome chains had any significant anti-tumor effect on U87-Luc tumors.

In mice treated by administration of magnetosome chains and multiple applications of the magnetic field, a slight increase in temperature is observed during the first three sessions of application of the field, which is similar for mice of groups 4 and 5 and which is 4° C. (first session), 2° C. (second session), and 0.5° C. (third session). No increase in temperature was observed in the following sessions of application of the field among mice belonging to groups 4 and 5. For all the other groups, no increase in temperature was observed. For mice belonging to group 5 with large tumors (~25 mm$^3$), a significant decrease in tumor volume during the 7 days following the administration of the magnetosome chains is observed, of 64%. Overall, the tumor volume increased significantly less for group 5 than for groups 1, 2, 3 and 6 during the 28 days following the administration of the magnetosome chains. In addition, mice belonging to group 5 live an average of one week longer than those of group 1, 2 and 6 mice. For 40% of mice belonging to group 4 with small tumors (~3 mm$^3$) the average tumor volume decreases during the 51 days following the administration of the magnetosome chains until the total disappearance of the tumor. These mice are totally healed. Indeed, these mice are still alive 143 days after the administration of the magnetosome chains (J143). The total cure of these mice was confirmed by the study of histological sections of their brains, taken at D143, showing the absence of tumors and lesions. For mice of group 7, treated with BNF-Starch, the increase of the average tumor volume and the time of 45 days were similar to those of mice of group 1, 2 and 6. No anti-tumor effect was observed.

We can conclude that: (i) for 40% of mice with an average volume of treated U87-Luc tumors of 3 mm$^3$, it is possible to entirely destroy these tumors by administering 40 µg in maghemite of a suspension of pyrogenic magnetosome chains extracted from AMB-1 in these tumors and by exposing these tumors to multiple applications of an alternating magnetic field with an average strength of 25 mT and a frequency of 198 kHz.

Example 3: Pyrogenic Chains of Magnetosomes Extracted from Strain MSR-1

Preparation:

MSR-1 bacteria are first cultured at 30° C. for 5 to 7 days on an agar gel in the presence of iron and a low concentration of oxygen (0.5% $O_2$). Magnetic colonies are collected and cultured at 30° C. in the presence of air for several days in an iron-free preculture medium comprising sources of carbon, nitrogen, minerals, trace elements and yeast extracts. The magnetotactic bacteria obtained from the preculture are grown in a fermenter of 50 liters at 30° C. in a medium similar to the preculture medium. During growth the pH is maintained at 6.8-7 by adding an acidic nutrient medium comprising an iron source and compressed air is introduced into the culture medium to promote bacterial growth while keeping the concentration in oxygen below 0.2% to allow the synthesis of the magnetosomes. MSR-1 bacteria issued from the fermentation are concentrated to an optical density, measured at 565 nm ($OD_{565nm}$), of 110-120. 100 ml of this bacterial concentrate are then mixed with 400 ml of 5M NaOH and heated at 60° C. for 1 h30 to 2 h to lyse the bacteria. The treated magnetosomes are then isolated from the bacterial debris by placing a Neodinium magnet overnight against the wall of the vessel comprising the suspension of lysed bacteria and by replacing the supernatant comprising sodium hydroxide and bacterial debris with 1×PBS. The suspension obtained is then sonicated for 20 seconds at 10 W in the presence of 1×PBS, placed against a Neodinium magnet for 15 minutes, the supernatant is removed and the treated magnetosomes are resuspended in 1×PBS. This sequence of sonication and magnetic separation is repeated four times. Pyrogenic chains of magnetosomes extracted from the MSR-1 strain are thus obtained.

Characterization:

The TEM measurements showed the presence in these suspensions of magnetosome chains with lengths between 200 and 1500 nm, magnetosome sizes between 20 nm and 60 nm. The absorption of the suspensions comprising 1 mg of iron of these chains, measured at 480 nm, decreases by 86% after 20 minutes, which shows the low stability of these suspensions. Light scattering measurements carried out on these chains indicate the presence of two populations of chains with hydrodynamic sizes 535 nm and 2822 nm. They have an isoelectric point of pH 6.4, a zeta potential which decreases from 15 mV at pH 2 to −31 mV at pH 12. The CHNS analysis reveals a carbon percentage in these chains of 4.1% deduced from the first measure and 12.2% on average deduced over the following 9 measures. In a second series of measurements, the endotoxin concentration of these suspensions, as measured by the LAL test, was estimated to be between 2000 and 17 000 UE per ml per mg of iron. The presence of endotoxins has also been suggested by Fourier transform infrared absorption measurements using a Nicolet FT-IR model 380 spectrometer. These spectra indicate the presence of peaks at 1150 cm$^{-1}$ and 1030 cm$^{-1}$, which can be attributed to the vibrations of phosphate groups of lipopolysaccharides and phospholipids. In a first series of measurements, when pyrogenic magnetosome chains extracted from MSR-1 are mixed with GL-261 cells and subjected to treatment condition 3, the temperature of the mixture increases by 9.4° C., from 36.2° C. before field application to 45.6° C. after 30 minutes of application of the field. The initial slope of the temperature variation is estimated at 0.012° C./sec during first measurement and at 0.019° C./sec during second measurement. This increase in temperature is greater than that observed with BNF-Starch. When this mixture is subjected to treatment condition 2, table 1 shows that the percentage of living cells is low at 5% in the first measurement and 12% in the second measurement and is lower than 39% obtained in condition 1 of treatment during first and second measurements, without field. This indicates the cytotoxicity induced by these pyrogenic magnetosomes on GL261 cells in the presence of treatment conditions 1 and 2 with a greater cytotoxicity for condition 2 (in the presence of the field) than for condition 1 (absence of the field).

Example 4: Central Parts of the Magnetosomes Derived from MSR-1

Preparation:

100 µl of the suspension comprising pyrogenic magnetosome chains extracted from the MSR-1 strain obtained in example 3 are mixed with 200 ml of a solution comprising 1% Triton X-100 and 1% SDS, the mixture is heated overnight at 50° C., placed against a Neodinium magnet, the supernatant is removed and replaced with 80 ml of phenol at pH 8. The obtained suspension is heated for 2 hours under sonication at 60° C., maintained overnight at 60° C. without sonication, placed against a magnet, the supernatant of the suspension was removed and replaced with 80 ml of chloroform. The suspension comprising the chloroform is placed against a Neodinium magnet, the supernatant is removed and the residual chloroform adsorbed at the surface of the treated magnetosomes is removed by heating these magnetosomes for 2 hours under a hood. Finally, the obtained central parts of the magnetosomes are desorbed from the glass wall of the tubes which comprise them by adding 80 ml of 1M NaOH heated for 1 hour at 60° C. in the sonicating bath. The suspension comprising the central parts of the magnetosomes is placed against a Neodinium magnet, the supernatant is removed and replaced with sterile MilliQ water, the suspension is sonicated for 20 seconds at 10 W. This washing sequence is repeated four times. The suspension comprising the central parts of the magnetosomes is degassed with nitrogen to avoid oxidation, sterilized by autoclaving and stored at −80 degrees.

Characterizations:

TEM measurements reveal the absence of coating surrounding the central parts of the magnetosomes. The absorption of the suspensions comprising 1 mg of the central part of the magnetosomes, measured at 480 nm, decreases by 60 to 80% after 20 minutes, which shows the low stability of these suspensions. The endotoxin concentration of these suspensions was estimated to be between 10 and 100 EU per milliliter per mg of iron oxide, which shows the pyrogenic nature of this suspension. The isoelectric point of these suspensions was measured at an acid pH of 3.5. Moreover, between pH 4 and pH 6, we observe an increase in the zeta potential from −8 mV to −1.5 mV, and between pH 6 and pH 8, we observe a decrease in zeta potential from −1.5 mV to −27 mV, which appears to be characteristic of the presence of aggregates. The light scattering measurements using the zetasizer reveal the presence of 79% aggregates of hydrodynamic spherical size 3076 nm and 21% aggregates of hydrodynamic spherical size 677 nm. CHNS analysis of these suspensions revealed carbon concentrations of 3.3%, nitrogen of 0.2%. These concentrations are lower than those measured for pyrogenic magnetosome chains extracted from MSR-1 (% N=0.7 and % C=4.1) and for lyophilized whole MSR-1 bacteria (% N=11 and % C=49). These results suggest that the quantity of organic material surrounding the central part of the magnetosomes is significantly lower in the sample comprising the central parts of the magnetosomes than in those comprising the whole MSR-1 bacteria or pyrogenic magnetosome chains extracted from MSR-1. The amine assay indicates that there are between 260 ng and 1.2 µg of amine functions in or at the surface of the central parts in the suspension comprising 1 mg in iron of the central parts. The phosphate assay indicates that there are 10 µg of phosphate function in or at the surface of the central part in the suspension comprising 1 mg in iron parts of the central part. In a second series of measurements, when the central parts of the magnetosomes are mixed with GL-261 cells and subjected to the treatment condition 3, the temperature of the mixture increases by 9.8° C. after 30 minutes of field application. The initial slope of the temperature variation is estimated as 0.012° C./sec. When this mixture is subjected to the treatment condition 2, table 1 shows that the percentage of living cells is low at 0-9% and lower than 77% obtained in treatment condition1, without field.

Example 5: Central Parts of Magnetosomes Derived from AMB-1

Preparation:

The culture of AMB-1 magnetotactic bacteria is carried out according to the process described in Example 3. After 7 days of culture, the bacteria are concentrated at 25° C. using tangential filtration (500 kDa column, 800 rpm) in a volume of 1 liter. They are then mixed with stirring in a solution comprising 1 mM EDTA and 30 µg/mL protamine at pH=7.4, the liquid medium is separated from the bacteria by tangential filtration, and then the bacteria obtained are mixed with a solution of PBS at pH=7.4, the liquid medium is again separated from the bacteria by tangential filtration. The obtained suspension of bacteria is then diluted in PBS to an optical density, measured at 565 nm, which allows lysing of the bacteria. The obtained suspension is sonicated for 30 minutes at 70 W at 0° C. using a titanium sonication probe having a diameter of 13 mm. The suspension thus obtained is washed a first time by placing a magnet against the wall of the container comprising the suspension, by removing the supernatant, by replacing it with a solution comprising 10 mM HEPES and 200 mM NaCl at 6° C. and by sonicating by series of 3 pulses at 30 W for 2 seconds. It was washed 4 more times using a similar method, replacing the mixture of HEPES and NaCl with sterile non-pyrogenic water. At the end of the washings, suspensions comprising magnetosome chains are obtained, as verified by TEM. The magnetosome chains are isolated from the supernatant by using a magnet, the supernatant is replaced by a volume of 30 ml of TRI REAGENT (Sigma, reference: T9424), the resulting solution is sonicated for 2 hours at 50° C. in an ultrasonic heating bath. The obtained suspension is then placed against a magnet at 4° C. for 1 hour, the supernatant is removed and replaced with a solution of sodium ethanoate and the mixture is sonicated for 30 minutes at 37° C. with an ultrasonic sonic heating bath. The treated magnetosomes are then washed a first time by isolating the supernatant with a magnet, by removing the supernatant, by replacing it with a solution of sodium ethanoate and then by sonicating the suspension for 30 min at 37° C. in an ultrasonic heating bath. This washing step is repeated 3 times in the same manner. In particular, to remove the lipid bilayer, the suspension is placed against a magnet, the supernatant is removed and replaced with a solution comprising 1% Triton X114, 1% deoxycholate and 4 mM EDTA. The suspension is then stirred mechanically for 1 hour at 4° C., placed against a magnet, the supernatant is removed and replaced with the solution comprising 1% Triton X114, 1% deoxycholate and 4 mM EDTA. The mixture is stirred for one hour at 37 degrees. The suspension is then washed a first time by placing a magnet against the wall of the vessel comprising the suspension, by removing the supernatant, by replacing it with a methanol/phosphate buffer (v/v, 1/1) mixture. Then, the obtained suspension is washed by being placed against a magnet, by removing the supernatant, by replacing it with a mixture comprising methanol and a phosphate buffer and by then sonicating the obtained suspension for 5 minutes at 30 W using a sonicating finger. A second wash is carried out in the same manner. The suspension is washed again by placing the suspension against a magnet, by removing the supernatant, by replacing it with sterile non-pyrogenic water and by sonicating with a sonicating bath at 37° C. for 1 hour.

5 additional washings with water are carried out in the same manner. The obtained suspension is then sterilized by autoclaving at 121° C. to obtain suspensions comprising the central parts of the magnetosomes derived from AMB-1.
Characterization:

TEM reveals the absence of coating surrounding the central parts of the magnetosomes. CHNS analysis of these suspensions revealed a carbon percentage of 4.9% which was significantly lower than that of the entire bacterium, which was 32%, and pyrogenic magnetosome chains (13.9%). The level of endotoxins in these central parts is 20 to 100 EU/mg/mL. The absorption of the suspensions comprising 1 mg of the central part of the magnetosomes, measured at 480 nm, decreases by 80 to 90% after 20 minutes, which shows the low stability of these suspensions. The zeta potential of these suspensions decreases overall from 38 mV at pH 2 to −60 mV at pH 12. The isoelectric point of these suspensions was measured at an acid pH of 4.9. In a second series of measurements, when the central parts of the magnetosomes are mixed with GL-261 cells and subjected to the treatment condition 3, the temperature of the mixture increases by 23.8° C. after 30 minutes of field application. The initial slope of the temperature variation is estimated as 0.024° C./sec. When this mixture is subjected to treatment conditions 2 and 1, the percentage of living cells is 48% and 30%, respectively.

Example 6: Central Parts of Magnetosomes Derived from MSR-1, Coated with Poly-L-Lysine Preparation:

The central parts of the magnetosomes derived from MSR-1 described in Example 4 are coated with poly-L-lysine under a laminar flow hood under sterile conditions. The poly (L-lysine hydrobromide) solution of molecular weight 21000 g/mol (Gmac, CAS: 25988-63-0) comprises 40 mg/ml of poly(L-lysine hydrobromide) prepared in non-pyrogenic water and filtered with a PES (polyethersulfone) filter of 0.45 μm, stored at −80° C. During the coating sequence, the mass of poly-L-lysine used is seven times greater than the mass of the central parts of the magnetosomes. 25 mL of a suspension comprising the central parts of the magnetosomes at an iron concentration of 3 mg/mL are introduced into a glass tube, the tube is positioned against a 1.3 T NdFeB magnet, the supernatant is removed, 25 ml of a suspension of poly(L-lysine hydrobromide) are then introduced into the tube at a final concentration of 20 mg/ml. The obtained suspension is then sonicated for 6 minutes at 4° C. using the sonicating finger at 10° C. The tube is stirred for 24 hours at 25° C. on a wheel at a speed of 13 rotations per minute at a temperature between 4 and 8° C., the suspension is sonicated using the sonicating finger for 10 seconds at 10 W. To carry out a first wash, the tube is then placed against the same magnet, the supernatant is removed and replaced by sterile MilliQ water. The suspensions are washed in this manner between 1 and 4 times. Finally, the obtained suspension is sonicated for 2 minutes at 24 W in ice at a temperature below 4° C. to avoid heating and the pH is adjusted to 6.8-7.2 with filtered KOH. A suspension comprising the central parts of the magnetosomes coated with poly-L-lysine is thus obtained.
Characterization:

Absorption of the suspension comprising 1 mg of the central parts of the magnetosomes coated with poly-L-lysine, measured at 480 nm, decreased by approximately 50% after 20 minutes, indicating the larger stability of this suspension compared with the suspension comprising the central parts of the uncoated magnetosomes. TEM images showed the presence of a poly-L-lysine coating around the central parts of these magnetosomes with a thickness of 4 to 16 nm, an average thickness of 8 nm and an arrangement in chains in part of these synthetic nanoparticles. An LAL assay carried out on these suspensions revealed a low endotoxin concentration of 78 EU per milliliter per mg of iron (recovery rate of 119%). The light scattering measurements carried out using the zetasizer reveal the presence of 92% aggregates of hydrodynamic spherical size 2489 nm and 8% spherical object having a hydrodynamic diameter of 137 nm which may correspond to the hydrodynamic diameter of the central parts of magnetosomes coated with poly-L-lysine. CHNS analysis revealed that the sample comprising 10 mg of the central parts of the poly-L-lysine coated magnetosomes comprised percentages of nitrogen of 0.4%, carbon of 3.6%, hydrogen of 0.6%, sulfur of 0.03%. The sample comprising 10 mg of lyophilized poly-L-lysine comprises 13% nitrogen, 33% carbon, 3.2% hydrogen, 0.03% sulfur. These results indicate a lower concentration of carbon in the suspensions comprising the central parts of magnetosomes, coated or not with poly-L-lysine, than in those comprising whole bacteria or pyrogenic magnetosome chains extracted from MSR-1. This suggests the presence of less organic material in the suspensions comprising the coated or uncoated magnetosome central parts than in those comprising the whole bacteria or pyrogenic magnetosome chains extracted from MSR-1. The presence of the poly-L-lysine coating around the central parts of the magnetosomes is suggested by the lower percentage of carbon in the sample comprising the central parts of the uncoated magnetosomes (% C=3.3%) than in that comprising the central parts of the magnetosomes coated with poly-L-lysine (% C=3.6%). When 1.5 mg of a suspension comprising the central parts of the magnetosomes coated with poly-L-lysine are mixed with 100 μl of 1% agar and the obtained mixture is subjected to the application of an alternating magnetic field of average strength 32 mT and frequency 198 kHz, the mixture reaches a heating temperature of 43° C. after 175 seconds. Gels comprising 1.5 mg of chemical nanoparticles (Micromod BNF-Starch, reference 10-00-102, and Micromod M-PEI, reference 17-00-152), mixed with 100 μl of 1% agar are subjected to the same alternating magnetic field. They reach a temperature of 43° C. after 600 seconds, which shows better heating properties for the suspensions comprising the central parts of magnetosomes coated with poly-L-lysine than for those comprising chemical nanoparticles BNF-Starch and M-PEI. When the central parts of magnetosomes coated with poly-L-lysine are mixed with GL-261 cells and the mixture is subjected to condition 3, the temperature of the mixture increases by 11.5° C., from 37° C. before application of the field to 48.5° C. after 30 minutes of application of the field. The initial slope of the temperature variation is estimated as 0.024° C./sec. When the same mixture is subjected to treatment condition 2, the percentage of living cells is 53% whereas it is only 23% without application of the field (treatment condition 1). This indicates the cytotoxicity induced by the suspensions comprising the central parts of magnetosomes coated with poly-L-lysine on the GL261 cells in the presence of the magnetic field.
Cytotoxicity:

An MTS (3-(4,5-dimethylthiazol-2-yl)-5-(3-carboxymethoxyphenyl)-2-(4-sulfophenyl)-2Htetrazolium) cytotoxicity test according to ISO 10993-5, is carried out by an approved organism under sterile conditions on L929 mouse fibroblasts using suspensions comprising the central parts of the magnetosomes coated with poly-L-lysine at concentrations of 0.01 mg/mL, 0.1 mg/mL, 0.5 mg/mL, and 1 mg/ml in iron comprised in EMEM10 medium. These suspensions are first incubated with L929 cells at 37° C. in the presence of 5% CO2 for 24 to 26 hours. After incubation, 20 µL of a staining solution comprising MTS and the phenazine methosulfate (PMS) agent are added to the cells. The cells are then incubated again for 120 to 135 minutes at 37° C. in the presence of 5% $CO_2$. The staining, resulting in an absorption at 492 nm, enables to demonstrate the viability of the cells. An observation of the cells under a microscope makes it possible to confirm or invalidate the viability of the cells. The results obtained show a percentage of living cells of 100%, 92% and 89% for the suspensions comprising the central parts of magnetosomes coated with poly-L-lysine at concentrations of 0.5 mg/mL, 0.1 mg/mL, and 0.01 mg/mL in iron, this indicates the absence of cytotoxicity of these suspensions at these concentrations. For a concentration of 1 mg/ml, it was not possible to conclude.

Pyrogenicity:

In order to confirm the absence of pyrogenicity of the suspension comprising the central parts of the poly-L-lysine-coated magnetosomes, suggested by the results of the LAL test, a pyrogenic test was carried out on a rabbit, according to ISO 10993-11, by an approved body. To this end, the suspension comprising the central parts of magnetosomes coated with poly-L-lysine at an iron concentration of 5 mg/ml was placed in the ultrasonic bath for 2 minutes, 1 ml of this suspension was diluted in 119 ml of NaCl 0.9%. The temperature of the suspension was maintained at 37° C. for 30 minutes, the suspension was homogenized and administered to three rabbits at a dose of 10 ml/kg intravenously. The body temperature of the three rabbits was measured every 30 minutes for 3 hours. It increases by 0.02° C. (first rabbit), 0° C. (second rabbit) and 0.22° C. (third rabbit). None of the three rabbits shows a temperature increase larger than 0.5° C. and the sum of the temperature increases in the three rabbits, which is 0.24° C., is less than 2.65° C. The product tested is therefore not pyrogenic according to the criteria of the European and American pharmacopoeias.

Acute Toxicity:

Acute systemic toxicity tests are performed among 6-week-old C57BL/6 female mice by administering 100 µl of suspensions comprising the central parts of the poly-L-lysine coated magnetosomes at a concentration of 0 mg, 0.5 mg, 1 mg, 2 mg, 4 mg and 8 mg in iron in the tail of mice. The body weight of each mouse, measured daily during 12 days after injection, remains stable, indicating that the maximum dose tolerated by mice is larger than 8 mg, i.e. about 400 mg/kg.

Anti-Tumor Efficacy on GL261 Tumors Implanted Subcutaneously in Mice:

Using a 1 mL 25 g syringe, a volume of 50 µl comprising $2.10^6$ cells of murine glioblastoma GL261 is administered subcutaneously on the left flank between the paw and the back of female mice black 6 C57BL/J. The tumors grow for 10 to 15 days until they reach a size between about 40 and 150 mm³. When the tumors have reached this size, the mice are anesthetized with isoflurane gas and maintained at 37° C. by means of hot plates. Using a Hamilton 250 µl syringe, 50 µl of two different non-pyrogenic suspensions are administered at the center of tumors comprising: (1), 5% glucose, (2), the central parts of the magnetosomes coated with poly-L-lysine at a concentration of 50 mg/mL in iron, mixed with 5% glucose. The suspension 2 is administered at a quantity, measured in µg of iron, equal to 20.t, where t is the size of the treated tumors in mm³. Then, the mice are exposed (or not) for 30 minutes to an alternating magnetic field of frequency 198 kHz and average intensity strength between 9 mT and 28 mT to maintain the intratumor temperature at a value between 43° C. and 46° C. during the first three field sessions. During the following sessions of application of the field, the average strength of the alternating magnetic field is fixed at 28 mT. The intratumor temperature is measured using a thermocouple. The sessions of application of the magnetic field are repeated 3 times per week, 15 times in total. Mice whose tumors continue to increase following two sessions of heating undergo a second administration of the suspension (2). Tumor sizes are measured with a caliper and the tumor volumes are estimated using the formula $V_{tumoral}=0.5 (L.1^2)$, where L and 1 represent the length and width of the tumors, respectively. The mice are euthanized when the tumor volume exceeds 1000 mm³ and/or when the weight of the mice has decreased by more than 20% from one measurement to another. According to this protocol, survival and tumor volume monitoring curves are performed during 71 days after administration of the nanoparticle suspensions.

It is observed that 5 out of 10 mice treated with the central parts of the poly-L-lysine coated magnetosomes and several applications of the magnetic field are totally cured 15 days after the beginning of the heating sessions. In these mice, there is no visible trace of the tumor or its sequelae (crust or scar). The remaining 5 mice treated with the central parts of the coated magnetosomes and application of the magnetic field, which are not totally cured, are euthanized about 30 days after the beginning of treatment. The mice treated with the central parts of the poly-L-lysine coated magnetosomes without application of the magnetic field are all euthanized about 12 days after the beginning of treatment. The survival rates, 50 days after the beginning of treatment, are 60% for the mice treated with the suspension comprising the central parts of the coated magnetosomes and application of the alternating magnetic field and 0% for the mice treated with the suspension comprising the coated central parts without field application. Without application of the magnetic field, all mice died less than 20 days after initiation of treatment.

Anti-Tumor Efficacy on U87 Tumors Implanted in Mouse Brain:

The protocols for administration of the tumor cells and for monitoring the mice are identical to those described in Example 3. 6 days after administration of the U87-Luc tumor cells in the mouse brain, when the tumors reach a size between 0.8 and 2 mm³, 2 µl of two different suspensions are administered at coordinates (0.2.2) in brains of anesthetized mice. For Groups 1 and 2, comprising 9 mice each, the mice received a suspension comprising the central parts of the poly-L-lysine coated magnetosomes at an iron concentration of 250 mg/mL mixed with 5% glucose. For groups 3 and 4, comprising 9 mice each, mice were given a suspension comprising 5% glucose. Group 1 and 3 mice are not exposed to a magnetic field. Groups 2 and 4 are exposed for 30 minutes to an alternating magnetic field of average strength 25 mT and frequency of 198 KHz three times per week for 6 weeks. For group 2, 4 mice with tumors regrowth receive an additional treatment 8 weeks after implantation of the U87-Luc cells consisting in a second administration of 2 µl of the suspension comprising the central parts of the poly-L-lysine coated magnetosomes at an iron concentration of 147 mg/mL mixed with 5% glucose and application of the alternating magnetic field of average strength 25 mT and frequency of 198 KHz three times per week for 3 weeks. Variations in temperature are measured during the different treatments using an infrared camera.

In mice treated by administration of the suspensions comprising the central parts of the poly-L-lysine coated magnetosomes and by multiple applications of the alternating magnetic field an increase in temperature was observed during the first sixteen field application sessions for the mice of group 2, which is in average 8° C. (first 3 sessions), 5° C. (12 following sessions), and 1° C. (16th session). No increase in temperature was observed in the following sessions of application of the field for the mice of group 2. For the four mice of group 2 which had been further treated following the 16th heating sessions due to the total disappearance of the tumor, a temperature increase of 5.5° C. is observed during the 9 additional sessions of application of the field. For groups 1, 3 and 4, no increase in temperature was observed.

In mice of groups 3 and 4, the tumor volumes increase rapidly to reach an average volume of 200 mm$^3$ in less than 45 days following the administration of the tumor cells. The mean survival times of mice of groups 3 and 4 were estimated to be 40 days on average following the administration of the tumor cells, suggesting that the only application of the alternating magnetic field has no anti-tumor effect. For mice of group 1, the tumor volume increased by an average of 5 mm$^3$ per week, much less than in groups 3 and 4. In addition, 13 weeks after implantation of U87-Luc cells, 50% of mice of group 1 are alive, having an average tumor volume of 56 mm$^3$. The treatment of mice of group 1 by the sole administration of a suspension comprising the central parts of magnetosomes coated with poly-L-lysine enables to slower tumor growth and to improve the survival compared with mice of groups 3 and 4. The mean tumor volume decreases during the 85 days following the administration of a suspension comprising the central parts of magnetosomes coated with poly-L-lysine until the total disappearance of the tumor which is observed 42 days following the administration of these suspensions (J42) for 66% of the mice. For the 4 mice in group 2 who received a second treatment because of the non-disappearance of the tumors, the tumor disappeared completely 20 days after the beginning of the second treatment. Overall, 91 days after administration of U87-Luc cells, all mice of group 2 are still alive and do not show bioluminescence signal, suggesting cure.

We can conclude that: (i), when the suspensions comprising the central parts of the magnetosomes coated with poly-L-lysine are administered in U87-Luc tumors, tumor growth is slowed down, which could be explained by the high concentration of or by the presence of poly-L-lysine, (ii), when these same suspensions are administered in U87-Luc tumors and subjected to multiple applications of an alternating magnetic field of 198 kHz frequency and average strength 25 mT, it is possible to completely eliminate these tumors.

Example 7: Central Parts of Magnetosomes Derived from MSR-1 Coated with Chitosan Preparation:
A suspension comprising 1 mg of the central part of the magnetosomes mixed with sterile non-pyrogenic water is sonicated for 5 minutes with a sonicating finger at a power of 5 W with pulses of 0.1 second, separated by intervals of 0.1 second. 0.25 mg of chitosan (chitosan hydrochloride CRS, reference sigma Y0000104) is mixed with the suspension comprising 1 mg the central part of the magnetosomes and the pH of the suspension is adjusted to 6.2 with 1M NaOH. The obtained mixture is sonicated with the sonicating finger at a power of 5 W, with pulses of 0.1 seconds, separated by intervals of 0.1 seconds, for 60 minutes at 45° C., then for 15 minutes at 60° C., then for 15 minutes at 70° C. The obtained suspension is washed a first time by placing a Neodinium magnet against the wall of the glass tube which comprises the suspension, by removing the supernatant and by replacing it with sterile non-pyrogenic water. It is washed a second time in the same manner.

Characterization:
The endotoxin level of these magnetosomes coated with chitosan is 25 EU/mg/mL. The absorption, measured at 480 nm, of a suspension comprising 1 mg of the central parts of magnetosomes coated with chitosan decreased by 3% during the 20 minutes of measurement, which shows the stability of this suspension. TEM measurements carried out on the central parts of magnetosomes coated with chitosan indicate an arrangement of these synthetic nanoparticles in chain, the presence of aggregates and a coating surrounding the central parts of the magnetosomes with an average thickness of 6 nm. When a suspension comprising the central parts of magnetosomes coated with chitosan is mixed with GL-261 cells and the mixture is subjected to treatment condition 3, the temperature of the mixture increases by 8.5° C. The initial slope of the temperature variation is estimated as 0.009° C./sec. during a first series of measurements. When this same mixture is subjected to treatment condition 2, the percentage of living cells is 0-5% whereas it is 20% in the absence of field (treatment condition 1). This shows the destruction efficacy of tumor cells by the central parts of magnetosomes coated with chitosan in treatment condition 2. The isoelectric point of these magnetosomes is estimated at pH 11. The zeta potential varies between 46 mV at pH 2 to −55 mV at pH 12. The hydrodynamic sizes of these magnetosomes are estimated at 273 nm for 7% and 1908 nm for 93% of them. The CHNS analysis indicates that their carbon percentage is 3.2%, close to the 3.3% carbon percentage measured for uncoated magnetosomes.

Example 8: Central Parts of the Magnetosomes Derived from MSR-1, Coated with Carboxy-Methyl-Dextran Preparation:
A suspension comprising 1 mg of the central part of the magnetosomes mixed with sterile non-pyrogenic water is sonicated for 5 minutes with the sonicating finger at a power of 5 W with pulses of 0.1 seconds, separated by intervals of 0.1 second. 4 mg of carboxy-methyl-dextran (reference SIGMA 86524-10G-F) are mixed with 1 mg of the central part of the magnetosomes and the pH of the mixture is adjusted to 3.5 with 1 M hydrochloric acid. The resulting mixture is sonicated for 60 minutes at 45 degrees using the sonicating finger at a power of 5 W, with pulses of 0.1 seconds, separated by 0.1 second intervals. The obtained suspension is washed three times. For the first wash, a magnet is placed against the wall of the tube, the supernatant is removed and replaced by sterile non-pyrogenic water. The obtained suspension is washed a second, then a third time in the same manner.

Characterization:
In a first series of measurements, the absorption, measured at 480 nm, of a suspension comprising 1 mg of the central parts of the magnetosomes coated with carboxy-methyl-dextran does not decrease during the 20 minutes of measurement, which shows the stability of this suspension. The TEM measurements enable to estimate a thickness of the coating surrounding the central parts of the magnetosomes between 2 and 20 nm. The light scattering measurements of the suspensions comprising the central parts of the magnetosomes coated with carboxy-methyl-dextran reveal the presence of 79% spherical objects with hydrodynamic diameter 1359 nm (population 1), 6% spherical objects with hydrodynamic diameter 5124 nm (population 2) and 15% of spherical objects with a hydrodynamic diameter of 331 nm (population 3). The size of the population 3 could correspond to that of the central parts of the magnetosomes coated with carboxy-methyl-dextran. The isoelectric point is estimated to be pH=3.4 and the zeta potential decreases by 20 mV at pH=2 to −31 mV at pH=12. When a suspension comprising the central parts of the magnetosomes coated with carboxy-methyl-dextran is mixed with GL-261 cells and the mixture is subjected to treatment condition 3, the temperature of the mixture increases by 29° C. The initial slope of the temperature variation is estimated as 0.023° C./sec. When this same mixture is subjected to the treatment condition 2, the percentage of living cells is 11% whereas it is 63% in the absence of field (treatment condition 1). This shows the destruction efficacy of the tumor cells by the central parts of the magnetosomes coated with citric acid using treatment condition 2. The percentage of carbon measured with the CHNS in these magnetosomes is 3.7%.

Example 9: Central Parts of Magnetosomes Derived from MSR-1, Coated with Citric Acid Preparation:

A suspension comprising 50 mg of the central parts of the magnetosomes mixed with 4.5 ml of sterile non-pyrogenic water is sonicated for 5 minutes with the sonicating finger at a power of 5 W with pulses of 0.1 seconds separated by intervals between pulses of 0.1 seconds. 20 mg of this suspension, comprised in a volume of 1.8 ml, are mixed with 35 mg of citric acid monohydrate (reference Sigma 33114-500G) comprised in 8 ml of sterile non-pyrogenic water. In this preparation, the mass of iron is 1.75 times larger than the mass of citric acid. The pH of the suspension is adjusted to 6 with 1 M sodium hydroxide, the obtained mixture is sonicated at 90° C. for one hour. The obtained suspension is washed a first time by placing a Neodinium magnet against the wall of the glass tube, by removing the supernatant and by replacing it with sterile non-pyrogenic water. It is washed a second time in the same manner.

Characterization:

The absorption, measured at 480 nm, of a suspension comprising 1 mg of the central parts of the magnetosomes coated with citric acid decreases by approximately 15% in 20 minutes, which shows the stability of this suspension. The TEM images of these synthetic nanoparticles reveal the presence of numerous chains, a good dispersion of these synthetic nanoparticles, low aggregation and the presence of a coating around the central part of these magnetosomes with a thickness of 1 to 15 nm. A LAL test, carried out on these suspensions, revealed a low endotoxin concentration of 19 EU per milliliter per mg of iron (recovery rate of 188%). CHNS analysis, carried out on these lyophilized suspensions, revealed a percentage of nitrogen of 0.8%, carbon of 3.7%, hydrogen of 0.3% and absence of sulfur. The sample comprising only lyophilized citric acid comprises a percentage of nitrogen of 0%, carbon of 36%, hydrogen of 4.7% and no sulfur. These results indicate a lower percentage of carbon in the suspensions comprising the central parts of the magnetosomes, whether or not coated with citric acid, than in those comprising the whole bacteria or pyrogenic magnetosome chains extracted from MSR-1. This may also suggest the presence of less organic material in suspensions comprising the central parts of the magnetosomes, whether or not coated with citric acid, than in those comprising whole bacteria or pyrogenic magnetosome chains extracted from MSR-1. The presence of the coating around the central parts of magnetosomes coated with citric acid is suggested by the lower percentage of carbon in the lyophilized suspension comprising the central part of the magnetosomes (% C=3.3%) than in the lyophilized suspension comprising the central parts of magnetosomes coated with citric acid (% C=3.7%). When a suspension comprising the central parts of the magnetosomes coated with citric acid is mixed with GL-261 cells and the mixture is subjected to the treatment condition 3, the temperature of the mixture increases by 25° C., from 35° C. before application of the field to 60° C. after application of the field. The initial slope of the temperature variation is estimated as 0.038° C./sec. When this same mixture is subjected to treatment condition 2, the percentage of living cells is 26% whereas it is 57% in the absence of field (condition 1 of treatment). This shows the destruction efficacy of the tumor cells by the central parts of the magnetosomes coated with citric acid in the treatment condition 2. The light scattering measurements of these suspensions reveal the presence of non-spherical objects, which may correspond to chains, of hydrodynamic size 788 nm. The isoelectric point is estimated to be pH=3.7 and the zeta potential decreases from 25 mV at pH=2 to −38 mV at pH=12.

Example 10: Central Parts of Magnetosomes Derived from MSR-1, Coated with Oleic Acid, Prepared According to the First Protocol Preparation:

We add to 5 mL of a suspension comprising 5 mg of the central part of the magnetosomes at a concentration of 1 mg/mL of iron, 10 μl of an ammonia $NH_4OH$ solution (25% in molecular weight) to obtain a pH between 10 and 11. The obtained suspension is sonicated in a water bath at 80° C. for 15 minutes with a sonicating finger at a power of 6-7 W with pulses of 0.2 seconds separated from each other by 0.5 seconds pauses. Then, either 267 μl of a 211 mM oleic acid solution (condition 1) or 50 μl of a 32 mM (0.4 mg) oleic acid solution (condition 2) are added. The mixture is then sonicated with the sonicating finger for 1 hour at a power of 6-7 W, with pulses of 0.2 seconds, separated by interval of pulses of 0.5 seconds. The obtained suspension is then washed with a Neodinium magnet which is placed against the glass tube comprising the suspension, the supernatant is removed and replaced by sterile non-pyrogenic water. The suspension is washed a second time, then a third and a fourth time in the same manner. After the last washing, aliquots are taken in order to carry out the various characterization tests. The suspension was kept at 4° C. until use.

Characterization:

The absorption, measured at 480 nm, of a suspension comprising the central parts of magnetosomes coated with oleic acid does not decrease for 20 minutes, indicating its stability. TEM images of the central parts of magnetosomes coated with oleic acid prepared according to Condition 2 demonstrated the presence of nanoparticle aggregates and a coating surrounding the central parts of the magnetosomes with a thickness of 0.5 to 5 nm. The light scattering measurements carried out on these coated magnetosomes, synthesized according to condition 2, reveal the presence of non-aggregated, stable spherical objects with a hydrodynamic diameter of 123 nm which can correspond to the hydrodynamic diameter of these coated magnetosomes. The isoelectric point is estimated at pH=3.5 and the zeta potential shows the presence of two populations whose zeta potential decreases for one population from 30 mV at pH=2 to −60 mV at pH=12 and for the other population from −10 mV at pH=6 to −35 mV at pH=12. When a suspension comprising the central parts of the magnetosomes coated with oleic acid is mixed with GL-261 cells and the mixture is subjected to treatment condition 3, the temperature of the mixture increases by 28° C. The initial slope of the temperature variation is estimated as 0.051° C./sec.

Example 11 Central Parts of Magnetosomes Derived from MSR-1, Coated with Oleic Acid, Prepared According to the Second Protocol Preparation:
The central part may be coated with oleic acid in the following manner We added to 1 mL of a suspension comprising 10 mg of the central parts of the magnetosomes at a concentration of 1 mg/mL in iron 100 mg of a solution of oleic acid at 10 mg/mL at pH 11. The obtained suspension is sonicated for 5 minutes with a sonicating finger at a power of 20 W, continuously and at ambient temperature. The suspension is then frozen at −80° C. for 30 minutes and then heated at 80° C. for 5 minutes. Then the mixture is sonicated with a sonicating finger for 1.5 hours at a power of 10 W, with pulses of 3 seconds, separated by intervals between pulses of 3 seconds. The obtained suspension is then washed with a Neodinium magnet which is placed against the glass tube comprising the suspension, the supernatant is removed and replaced by sterile non-pyrogenic water. The suspension is washed a second time and a third time in the same manner After the last washing, aliquots are taken in order to carry out the various characterization tests. The suspension was kept at 4° C. until use.
Characterization:
The properties of the central parts of magnetosomes coated with oleic acid may be as follows. The absorption, measured at 480 nm, of a suspension of the central parts of the magnetosomes coated with oleic acid comprising 1 mg of iron does not decrease for 20 minutes, indicating its stability. When a suspension comprising the central parts of magnetosomes coated with oleic acid is mixed with GL-261 cells and the mixture is subjected to treatment condition 3, the temperature of the mixture increases by 5° C. The initial slope of the temperature variation is estimated as 0.012° C./sec. When this mixture is subjected to treatment condition 2, the percentage of living cells is 14% whereas it is 53% in the absence of field (treatment condition 1). The percentage of carbon in these magnetosomes is 3.4%.

Example 12: Central Parts of Magnetosomes Derived from MSR-1, Coated with Folic Acid Preparation:
A suspension comprising 50 mg in iron of the central parts of the magnetosomes mixed with 4.5 mL of sterile non-pyrogenic water is sonicated for 5 minutes using the sonicating finger at a power of 30 W with pulses of 30 seconds, intervals of 10 seconds between pulses. A 1.8 mL volume, comprising 20 mg in iron of the central parts of the magnetosomes, is introduced into a 10 mL sterile glass tube placed against a magnet, the supernatant is removed and replaced with 8 mL of a solution at 2 mg/mL of folic acid (Fisher BioReagents, reference: 59-30-3) mixed with sterile non-pyrogenic water, previously adjusted to pH 9.5 with a 1 M solution of sodium hydroxide and sterilized by filtration (filter 0.45 μm). In this preparation, the mass of iron is 1.25 times larger than the mass of folic acid. The obtained mixture is sonicated for 1.5 hours with the sonicating finger at a power of 30 W with pulses of 30 seconds, separated by intervals between pulses of 10 seconds. The obtained suspension of volume 8 mL is comprised in a 10 mL glass tube. It is washed once by placing a Neodinium magnet against the wall of the glass tube, by removing the supernatant and then by replacing it with pyclerotic HyClone water and by sonicating for 1 minute at 30 W. It is washed four more times in the same manner.
Characterization:
The absorption, measured at 480 nm, of a suspension comprising 1 mg of the central parts of magnetosomes coated with folic acid does not decrease during 20 minutes, which shows the stability of this suspension. The diffusion measurements of this suspension show the presence of 90% of spherical aggregates with a hydrodynamic diameter of 2876 nm and 10% of spherical objects with a hydrodynamic diameter of 235 nm which could correspond to the magnetosomes coated with folic acid. The isoelectric point of this suspension was estimated to be pH 7.9 and the zeta potential decreased from 45 mV at pH 2 to −43 mV at pH 12. The thickness of the coating surrounding the central portions of these magnetosomes was measured to be 1 to 4 nm. When a suspension comprising the central parts of the magnetosomes coated with citric acid is mixed with GL-261 cells and the mixture is subjected to treatment condition 3, the temperature of the mixture increases by 20° C. The initial slope of the temperature variation is estimated as 0.042° C./sec. When this same mixture is subjected to treatment condition 2, the percentage of living cells is 9% whereas it is 93% in the absence of field (treatment condition 1). This shows the destruction efficacy of the tumor cells by the central parts of the magnetosomes coated with folic acid in treatment condition 2. The percentage of carbon in these magnetosomes is estimated at 3.9%.

Example 13: Central Parts of Magnetosomes Derived from MSR-1, Coated with DOPC

Preparation:
40 mg of DOPC (1,2-dioleoyl-sn-glycero-3-phosphocholine, reference Sigma: P6354) were solubilized in 100 μL of chloroform in a 10 mL glass tube and then the solvent was evaporated for 10 minutes using inert gas (nitrogen) to form a homogeneous lipid film in the tube. A suspension comprising the central parts of magnetosomes with 20 mg of iron mixed with 8 ml of sterile non-pyrogenic water, is introduced into the tube comprising the lipid film and is then sonicated for 1.5 hours with the sonicating finger at a power of 30 W with pulses of 10 seconds, separated by intervals of 0.5 seconds. During this preparation, the mass of DOPC is twice as high as the mass of iron. The obtained suspension is washed a first time by placing a Neodinium magnet against the glass tube wall, by removing the supernatant and then by replacing it with sterile nonpyrogenic water and by sonicating for 1 minute at 30 W. It is washed five more times in the same manner.
Characterization:
In a first series of measurements, the absorption, measured at 480 nm, of a suspension comprising the central parts of magnetosomes coated with DOPC does not decrease during the 20 minutes of measurement, which shows the stability of this suspension. The TEM images indicate the presence of a coating surrounding the central parts of these magnetosomes of thickness 0.6 to 3 nm. The light scattering measurements carried out on these suspensions reveal the presence of 87% spherical aggregates with a hydrodynamic diameter of 1871 nm and 13% of spherical objects with a hydrodynamic diameter of 278 nm which could correspond to the sizes of the central parts of the magnetosomes coated with DOPC. The isoelectric point is measured at pH 3 and the zeta potential decreases from 10 mV at pH 2 to −35 mV at pH 12. When a suspension comprising the central parts of the magnetosomes coated with DOPC is mixed with GL-261 cells and the mixture is subjected to treatment condition 3, the temperature of the mixture increases by 33.5° C. The initial slope of the temperature variation is estimated as 0.05° C./sec. When this same mixture is subjected to treatment condition 2, the percentage of living cells is 0-5% whereas it is 13% without application of the field (treatment condition 1). This indicates the cytotoxicity induced by the central parts of the DOPC-coated magnetosomes on GL261 cells in the presence of an alternating magnetic field. The percentage of carbon in these magnetosomes is estimated as 7.5%.

Example 14: Central Parts of Magnetosomes Derived from AMB-1, Coated with DOPC

Preparation:

In a 35 mL conical glass tube, 280 mg of DOPC (1,2-dioleoyl-sn-glycero-3-phosphocholine, reference Sigma: P6354) are solubilized in 500 μL of chloroform and then the solvent is evaporated during 15 minutes with nitrogen to form a homogeneous lipid film in the tube. A suspension comprising the central parts of the magnetosomes with 10 mg of iron mixed with 15 ml of sterile non-pyrogenic water is introduced into the tube comprising the lipid film and is then sonicated for 30 minutes with the sonicating finger at a power of 20 W with pulses of 10 seconds, separated by intervals between pulses of 20 seconds. During this preparation, the mass of DOPC is 28 times higher than the mass of iron. The resulting suspension was purified using a SEPHADEX G-25 size exclusion column (GE Healthcare, Buckinghamshire, UK). The brown colored suspension is collected and then concentrated by placing a Neodinium magnet against the glass tube wall, by removing a portion of the supernatant which is replaced by sterile non-pyrogenic water and by sonicating the sample for 1 minute at 30 W.

Characterization:

The TEM images of these suspensions enable to estimate coating thickness at 50 to 150 nm.

Example 15: Central Parts of Magnetosomes Derived from AMB-1, Coated with Alendronate Preparation:

A 2 mL volume, comprising 10 mg in iron, was introduced into a 25 mL glass tube (non-pyrogenic) and then placed against a magnet. The supernatant was removed and then replaced with 10 ml of a solution comprising 11.6 mg/ml alendronate mixed with sterile MilliQ water, previously adjusted to pH 2.5 with a 0.1 M solution of hydrochloric acid and sterilized by Filtration (0.45 μm filter). During this preparation, the mass of alendronate is 11.6 times higher than the mass of iron. The obtained mixture is continuously sonicated for 15 minutes at the sonicating finger with a power of 30 W. The suspension is then heated under a microwave at 70 W, 3 times during 1 minute with a 5 minutes interval, where the sample is cooled in an ice bath. The suspension is washed a first time by placing a Neodinium magnet against the glass tube wall, by removing the supernatant and then by replacing it with sterile MilliQ water and by sonicating for 1 minute at 30 W. It is washed ten times in the same manner by placing a Neodinium magnet against the glass tube wall, by removing the supernatant and then by replacing it with sterile MilliQ water and by sonicating for 1 minute at 30 W.

Characterization:

The measurements of the LAL test enable to estimate the quantity of endotoxins in these suspensions as between 53 and 144 EU/mg/mL. The absorption, measured at 480 nm, of a suspension of the central parts of magnetosomes coated with alendronate comprising 1 mg in iron decreased by 1% during the 20 minute measurement, demonstrating the stability of this suspension. TEM measurements indicate that a matrix surrounds these magnetosomes. These magnetosomes possess an isoelectric point of pH 3.5, hydrodynamic sizes of 527 nm for 14% of them and 2735 nm for 86% of them, a zeta potential which varies from 25 mV at pH 2 to −47 mV at pH 12. When a suspension comprising the central parts of magnetosomes coated with alendronate is mixed with GL-261 cells and the mixture is subjected to treatment condition 3, the temperature of the mixture increases by 18.3° C. The initial slope of the temperature variation is estimated as 0.28° C./sec. When this same mixture is subjected to treatment condition 2, the percentage of living cells is 2% whereas it is 17% without application of the field (treatment condition 1). This indicates the cytotoxicity induced by the central parts of magnetosomes coated with alendronate on GL261 cells in the presence of an alternating magnetic field. The percentage of carbon in these magnetosomes is estimated to be 9%.

Example 16: Central Parts of Magnetosomes Derived from MSR-1, Coated with Neridronate Preparation:

A suspension comprising 50 mg in iron of the central parts of the magnetosomes, mixed with 4.5 mL of sterile non-pyrogenic water, is sonicated for 5 minutes with the sonicating finger at a power of 30 W, with 30 seconds pulses separated by intervals between pulses of 10 seconds. A volume of 1.8 mL, comprising 20 mg in iron of the obtained suspension, is introduced into a 10 mL glass tube placed against a magnet, the supernatant of the suspension is removed and replaced with 8 mL of a solution comprising 20 mg/mL of neridronate mixed with sterile non-pyrogenic water and adjusted to pH 2.5. In this preparation, the mass of neridronate is 8 times higher than the mass of iron. The mixture obtained is sonicated for 2 hours using the sonicating finger at a power of 30 W, with pulses of 30 seconds, separated by intervals of 10 seconds. The suspension is washed a first time by placing a Neodinium magnet against the wall of the glass tube, by removing the supernatant and then by replacing it with sterile non-pyrogenic water previously adjusted to pH 11. It is washed five more times in the same way.

Characterization:

The absorption, measured at 480 nm, of the suspension comprising the central parts of the magnetosomes coated with neridronate does not decrease for 20 minutes, indicating the stability of this suspension. The TEM measurements indicate the presence of a coating around the central parts of the magnetosomes with a thickness of 19 to 200 nm. The light scattering measurements carried out on these suspensions indicate the presence of 1% of spherical aggregates with a hydrodynamic diameter of 5560 nm, of 59% of spherical aggregates with a hydrodynamic diameter of 710 nm, and of 40% of spherical objects of hydrodynamic diameter 207 nm that may correspond to the central parts of the magnetosomes coated with neridronate. When a suspension comprising the central parts of magnetosomes coated with neridronate is mixed with GL-261 cells and subjected to the treatment condition 3, the temperature of the mixture increases from 37.2° C. before application of the field to 43.9° C. after 30 minutes of field application. The initial slope of the temperature variation is estimated as 0.017° C./sec. When this same mixture is subjected to treatment condition 2, the percentage of living cells is 28% whereas it is 44% without application of the field (treatment condition 1). This indicates the cytotoxicity induced by the central parts of the magnetosomes coated with neridronate on the GL261 cells in the presence of treatment condition 2. The isoelectric point of these synthetic nanoparticles coated with neridronate is estimated at pH 3.5 and the zeta potential decreases from 40 mV at pH 2 to −42 mV at pH 12. The carbon percentage of these magnetosomes is estimated at 18.1%.

Example 17: Central Parts of Magnetosomes Derived from MSR-1, Coated with PEI

Preparation:

A suspension of magnetosome minerals comprising 50 mg in iron mixed with 4.5 mL of sterile non-pyrogenic water is sonicated for 5 minutes with the sonicating finger at a power of 30 W with pulses of 30 seconds separated by intervals of 10 seconds. A 1.8 mL volume comprising 20 mg in iron of this suspension is introduced into a 10 mL glass tube placed against a magnet. The supernatant is removed and replaced with 8 mL of a PEI solution at concentration 25 mg/mL, mixed with sterile non-pyrogenic water with a pH adjusted to 9.5. In this preparation, the mass of PEI is 10 times larger than the mass of iron. The obtained mixture is sonicated for 2 hours with the sonicating finger at a power of 30 W, with pulses of 30 seconds, separated by intervals of 10 seconds. The obtained suspension is washed a first time by placing a Neodinium magnet against the glass tube wall, by removing the supernatant, by replacing it with sterile non-pyrogenic water and by sonicating for 1 minute at 30 W. It is washed five more times in the same manner.

Characterization:

The absorption of the suspension comprising the central parts of magnetosomes coated with the PEI, measured at 480 nm, does not decrease during the 20 minutes of measurement, which shows the stability of this suspension. The TEM measurements indicate a coating thickness of 8 to 10 nm. The light scattering measurements of this suspension indicate the presence of spherical objects with a 175 nm hydrodynamic diameter which could correspond to the central parts of the magnetosomes coated with PEI. The isoelectric point is estimated at 11 and the zeta potential decreases from 42 mV at pH 2 to −16 mV at pH 12. The CHNS measurements show a nitrogen percentage of 1.1% and a carbon percentage of 4.5%, both larger than the nitrogen and carbon percentages of 0.2% and 3.3%, respectively, in the central parts of the uncoated magnetosomes, suggesting the presence of the coating. In a second series of measurements, when a suspension comprising the central parts of the magnetosomes coated with PEI is mixed with GL-261 cells and subjected to treatment condition 3, the temperature of the mixture increases from 37° C. before application of the field to 43° C. after 30 minutes of application of the field. The initial slope of the temperature variation is estimated as 0.014° C./sec. When this same mixture is subjected to treatment condition 2, the percentage of living cells is 15% whereas it is 40% without application of the field (treatment condition 1). This indicates the cytotoxicity induced by the central parts of magnetosomes coated with PEI on GL261 cells in the presence of treatment condition 2.

Example 18: Central Parts of Magnetosomes Derived from AMB-1, Coated with PEI

Preparation:

A suspension comprising 10 mg in iron of the central parts of the magnetosomes, mixed with 10 mL of sterile non-pyrogenic water, is sonicated for 5 minutes with the sonicating finger at 30 W with pulses of 30 seconds, separated by intervals of 10 seconds. This suspension is placed against a magnet, the supernatant is removed and then replaced with 10 mL of a PEI solution at 20 mg/mL, mixed with sterile non-pyrogenic water at pH 9.5. During this preparation, the mass of PEI is twice as high as the mass of iron. The obtained mixture is sonicated for 30 minutes with the sonicating finger at a power of 20 W with pulses of 10 seconds, separated by intervals between pulses of 20 seconds. The suspension is cooled every two minutes in an ice bath. It is washed once by placing a Neodinium magnet against the wall of the glass tube, by removing the supernatant and then by replacing it with pyclerotic HyClone water and by sonicating for 1 minute at 30 W. It is washed ten more times in the same manner.

Characterization:

The LAL test reveals an endotoxin concentration of less than 50 EU/mg/mL in these suspensions. The TEM measurements enable to estimate the thickness of the coating surrounding the central parts of these magnetosomes as between 4 and 18 nm. The absorption of the suspension of the central parts of magnetosomes coated with PEI comprising 1 mg in iron, measured at 480 nm, decreased by 64% during the 20 minutes of measurement. The light scattering measurements of this suspension indicate the presence of objects of hydrodynamic size 125 nm for 6% of them, 5445 nm for 1% of them and 1067 nm for 93% of them. The isoelectric point is estimated at 11.3 and the zeta potential decreases from 50 mV at pH 2 to −10 mV at pH 12. CHNS measurements reveal a carbon percentage of 6.6%. When a suspension comprising the central parts of magnetosomes coated with PEI is mixed with GL-261 cells and subjected to treatment condition 3, the temperature of the mixture increases by 12° C. after 30 minutes of application of the field. The initial slope of the temperature variation is estimated as 0.04° C./sec. When this same mixture is subjected to treatment condition 2, the percentage of living cells is 12% whereas it is 26% without application of the field (treatment condition 1). This indicates the cytotoxicity induced by the central parts of magnetosomes coated with PEI on GL261 cells in the presence of treatment condition 2.

Example 19: Central Parts of Magnetosomes Derived from MSR-1, Coated with Al(OH)$_3$ Preparation:

The suspension comprising 7 mg per milliliter of the central part of the magnetosomes is first sonicated for 5 minutes at a power of 5 W with pulses of 0.1 seconds and intervals between pulses of 0.1 seconds. A suspension comprising 2 mg of the central part of the magnetosomes is introduced in a 8 mL glass tube, the suspension is placed against a neodymium magnet, the supernatant is removed and replaced by 600 µl of aluminum hydroxide at 10 mg/mL. The mixture is sonicated for 90 minutes continuously at 20 W. A first wash is carried out by placing the suspension against a magnet, by removing the supernatant and by replacing it with HyClone water. Three additional washes were carried out in the same manner.

Characterization:

The absorption of the suspension comprising the central parts of the magnetosomes coated with $Al(OH)_3$, measured at 480 nm, does not decrease during the 20 minutes of measurement, which shows the stability of this suspension. TEM measurements reveal the presence of a gel surrounding the central parts of these magnetosomes. The light scattering measurements of this suspension indicate the presence of objects of hydrodynamic size 204 nm for 5% of them and 1810 nm for 95% of them. The isoelectric point is estimated to be pH 2.5 and the zeta potential decreases from 5 mV at pH 2 to −30 mV at pH 12. CHNS measurements reveal a carbon percentage of 3.3%. When a suspension comprising the central parts of the magnetosomes coated with $Al(OH)_3$ is mixed with GL-261 cells and subjected to treatment condition 3, the temperature of the mixture increases by 21.3° C. after 30 minutes of field application. The initial slope of the temperature variation is estimated as 0.034° C./sec. When this same mixture is subjected to treatment condition 2, the percentage of living cells is 26% whereas it is 91% without application of the field (treatment condition 1). This indicates the cytotoxicity induced by the central parts of the central parts of the magnetosomes coated with $Al(OH)_3$ on the GL261 cells in the presence of treatment condition 2.

Example 20: Central Parts of Magnetosomes Derived from MSR-1, Coated with Silica (APTS)

Preparation:

The suspension comprising 7 mg per milliliter of the central part of the magnetosomes is first sonicated for 5 minutes at a power of 5 W with pulses of 0.1 seconds and intervals between pulses of 0.1 seconds. A suspension comprising 10 mg of the central part of the magnetosomes is introduced in a 8 mL glass tube, the suspension is placed against a neodymium magnet, the supernatant is removed and replaced with 2 mL of a mixture of hexane and absolute ethanol (1:1; v/v). The suspension is sonicated for a few minutes before addition of 200 µL of APTS ((3-Aminopropyl) triethoxysilane, APTS; Sigma reference: 440140), i.e. 211 mg and 500 µL of 5M NaOH. The mixture is sonicated for 10 minutes at 85° C. at a power of 5 W with pulses of 0.1 seconds and intervals between pulses of 0.1 seconds. A first wash is carried out by placing the suspension against a magnet, by removing the supernatant and by replacing it with a volume of 1.5 mL of a mixture of hexane and absolute ethanol (1/1; v/v). Then the suspension is sonicated for 30 seconds at a power of 5 W with pulses of 0.1 seconds and intervals between pulses of 0.1 seconds. Three additional washes were carried out in the same manner. Then a volume of 1 milliliter of 5M sodium hydroxide is added to the suspension of nanoparticles and then the mixture is sonicated for 15 minutes at 80° C. at a power of 5 W with pulses of 0.1 second and intervals between pulses of 0.1 seconds. A first wash is carried out by placing the suspension against a magnet, by removing the supernatant and by replacing it with HyClone water. Two additional washes were carried out in the same manner.

Characterization:

The absorption of the suspension of the central parts of magnetosomes coated with silica comprising 1 mg of iron, measured at 480 nm, decreases by 90% during the 20 minutes of measurement. TEM measurements reveal the presence of a gel surrounding the central parts of these magnetosomes. The light scattering measurements of this suspension indicate the presence of objects of hydrodynamic size 235 nm for 10% of them, 277 nm for 7% of them and 1986 nm for 93% of them. The isoelectric point is estimated to be pH 6.7 and the zeta potential decreases from 39 mV at pH 2 to −31 mV at pH 12. CHNS measurements reveal a carbon percentage of 7.4%. When a suspension comprising the central parts of the magnetosomes coated with silica is mixed with GL-261 cells and subjected to treatment condition 3, the temperature of the mixture increases by 26.9° C. after 30 minutes of application of the field. The initial slope of the temperature variation is estimated to be 0.1° C./sec. When this same mixture is subjected to treatment condition 2, the percentage of living cells is 2.5% whereas it is 40% without application of the field (treatment condition 1). This indicates the cytotoxicity induced by the central parts of the magnetosomes coated with silica on GL261 cells in the presence of treatment condition 2.

Example 21: Different Coating Protocols

From the protocols described in Examples 6 to 20, it may be possible to coat the central part of the magnetosomes with coating agents poly-L-lysine, chitosan, carboxy-methyl-dextran, citric acid, oleic acid, silica, folic acid, DOPC, alendronate, neridronate, PEI, $Al(OH)_3$ using for the mixture of the central parts and the coating agent a ratio between coating mass and central part mass between $10^{-9}$ and $10^9$, $10^{-6}$ and $10^6$, or between $10^{-2}$ and $10^2$, a sonication time between $10^{-9}$ and $10^9$ seconds, between $10^{-6}$ and $10^6$ seconds, or between $10^{-2}$ and $10^2$ seconds or a sonication power between $10^{-9}$ and $10^9$ W, between $10^{-6}$ and $10^6$ W, or between $10^{-2}$ and $10^2$ W.

Example 22: Binding Properties Between the Central Parts

TEM measurements carried out on central parts coated with different coatings (PEI, DOPC, Neridronate, Chitosan, citric acid, dextran, $AlOH_3$, silica, folic acid) reveal that the distance separating the outer surface of two central parts separated by bonding material is between 0 and more than 400 nm, that the number of central parts linked together by bonding material is between 2 and more than 10,000, that the central parts linked together by bonding material form different shapes such as chains, circles, rhombuses, quadrilaterals (table 3), that the chains are characterized by the presence of different central parts whose facets are parallel, suggesting an alignment of the crystallographic axes of the different central parts in the direction of elongation of the chains.

TABLE 1

| Sample | Coating | Species | Pyrogenicity (LAL test) Endotoxin concentration (UE/mg/mL) | Stability (Δabs at 480 nm) Δabs (%) | ΔT (° C.) | δT/δt (° C.·s$^{-1}$) | % living cells (−B) | % living cells (+B) |
|---|---|---|---|---|---|---|---|---|
| BNF-Starch | hydroxyethyl starch | chemical | <50 | 0 | 6.2 | 0.009 | 71 ± 5 | 78 ± 5 |
| BNF-Starch | hydroxyethylstarch | chemical | | 0 | 7.6 | 0.01 | 86 | 31 |
| Whole bacteria | | AMB-1 | | | | | | |
| Whole bacteria | | MSR-1 | | | | | | |
| Pyrogenic Extracted chains | bacterial membrane | AMB-1 | 18000-150000 | 30 | 20.5 | 0.043 | | |
| Pyrogenic extracted chains | bacterial membrane | AMB-1 | | | 9.8 | 0.012 | 55 | 10 |
| Pyrogenic extracted chains | bacterial membrane | MSR-1 | 2000-11300 | | 9.4 | 0.019 | 39 ± 5 | 5 ± 5 |
| Pyrogenic extracted Chains | Bacterial membrane | MSR-1 | 2000-17000 | 86 | | 0.012 | 39 | 12 |
| Central parts of magnetosomes | None | AMB-1 | | 80-90 | | | | |
| Central parts of magnetosomes | None | AMB-1 | 20 to 100 | 66-93 | 23.8 | 0.024 | 30 | 48 |
| Central parts of magnetosomes | None | MSR-1 | 10 to 100 | 60-80 | | | | |
| Central parts of magnetosomes | None | MSR-1 | | | 9.8 | 0.012 | 77 | 0 to 9 |
| Central parts of magnetosomes | Poly-L-lysine | MSR-1 | 78 | 50 | 11 | 0.024 | 53 ± 5 | 23 ± 5 |
| Central parts of magnetosomes | Poly-L-lysine | MSR-1 | | 30 | | | | |
| Central parts of magnetosomes | Chitosan | MSR-1 | | 3 | 8.5 | 0.009 | 20 ± 5 | 0 ± 5 |
| Central parts of magnetosomes | Chitosan | MSR-1 | 25 | | | 0.014 | | |
| Central parts of magnetosomes | Carboxy-methyldextran | MSR-1 | | 0 | 28.8 | 0.023 | 63 ± 5 | 11 ± 5 |
| Central parts of magnetosomes | Carboxy-methyldextran | MSR-1 | | 10 | | | | |
| Central parts of magnetosomes | Citric acid | MSR-1 | 19 | 15 | 25.2 | 0.038 | 57 ± 5 | 26 ± 5 |
| Central parts of magnetosomes | Citric acid | MSR-1 | | | | | 57 | 7 |
| Central parts of magnetosomes | Oleic acid | MSR-1 | | 0 | 28.4 | 0.051 | | |
| Central parts of magnetosomes | Oleic acid | MSR-1 | | 0 | 5 | 0.012 | 53 | 14 |

| Sample type | Coating | Species | Pyrogenicity (LAL test) Endotoxin concentration (UE/mg/mL) | Stability (Δabs à 480 nm) Δabs (%) | ΔT (° C.) | δT/δt (° C.·s$^{-1}$) | % living cells (−B) | % living cells (+B) |
|---|---|---|---|---|---|---|---|---|
| Central part of magnetosomes | Silica | MSR-1 | | | | | | |
| Central part of magnetosomes | Silica | MSR-1 | | 90 | 26.9 | 0.100 | 40 | 2.5 |
| Central part of magnetosomes | Folic acid | MSR-1 | | 0 | 20 | 0.042 | 93 ± 5 | 9 ± 5 |
| Central part of magnetosomes | DOPC | MSR-1 | | 0 | 33.5 | 0.049 | 13 ± 5 | 0 à 5 |
| Central part of magnetosomes | DOPC | MSR-1 | | 2-70 | | | | |
| Central part of magnetosomes | DOPC | AMB-1 | | | | | | |
| Central part of magnetosomes | Alendronate | AMB-1 | 53-144 | | | | | |
| Central part of magnetosomes | Alendronate | AMB-1 | | 1 | 18.3 | 0.028 | 17 | 2 |
| Central part of magnetosomes | Neridronate | MSR-1 | | 0 | 6.7 | 0.017 | 44 ± 5 | 28 ± 5 |
| Central part of magnetosomes | PEI | MSR-1 | | 0 | 6 | 0.014 | 40 ± 5 | 19 ± 5 |
| Central part of magnetosomes | PEI | AMB-1 | <50 | | | | | |

TABLE 1-continued

| | | | | | | | |
|---|---|---|---|---|---|---|---|
| Central part of magnetosomes | PEI | AMB-1 | | 64 | 12 | 0.040 | 26 | 12 |
| Central part of magnetosomes | Al(OH)$_3$ | MSR-1 | | 0 | | | | |
| Central part of magnetosomes | Al(OH)$_3$ | MSR-1 | | | 21.3 | 0.034 | 91 | 26 |

TABLE 2

| Sample properties | | | Coating thickness | Isoelectric point | Hydrodynamic sizes of populations | Zeta potential (mV) | | |
|---|---|---|---|---|---|---|---|---|
| Sample type | Coating | Species | (nm) | (pH) | (nm) | pH 2 | pH 4 | pH 6 |
| BNF-Starch | starch | | | | | | | |
| BNF-Starch | Hydroxyethyl-starch | chemical | 1 to 4 | 9.5 | 117 | 7 | 6 | 6 |
| Whole bacteria | | AMB-1 | | | | | | |
| Whole bacteria | | AMB-1 | | | | | | |
| Whole bacteria | | MSR-1 | | | | | | |
| Pyrogenic extracted chains | Bacterial membrane | AMB-1 | 1 to 5 | 4.2 | | 20 | 2.5 | −18 |
| Pyrogeinc extracted chains | Membrane bacterianne | AMB-1 | | | 986 (81%) 4363 (14%) 176 (5%) | | | |
| Pyrogenic extracted chains | Bacterial membrane | MSR-1 | 1 to 5 | | | | | |
| Pyrogenic extracted chains | Bacterial membrane | MSR-1 | | 6.4 | 2822 (82%) 535 (18%) | 15 | 14 | 3 |
| Central parts of magnetosomes | None | AMB-1 | 0 | 4.9 | | 38 | 40 | −55 |
| Central parts of magnetosomes | None | AMB-1 | | | 752 (97%) 5253 (3%) | | | |
| Central parts of magnetosomes | None | MSR-1 | 0 | 3.5 | 3076 (79%) 677 (21%) | 18 | −8 | −1.5 |
| Central parts of magnetosomes | Poly-L-lysine | MSR-1 | 4 to 16 | 8.7 | 2489 (92%) 137 (8%) | 43 | 35 | 24.5 |
| Central parts of magnetosomes | Chitosan | MSR-1 | 6 | | | | | |
| Central parts of magnetosomes | Chitosan | MSR-1 | | 11 | 1908 (93%) 273 (7%) | 46 | 31 | 30 |
| Central parts of the magnetosomes | Carboxy-methyldextran | MSR-1 | 2 to 20 | 3.4 | 5124 (6%) 1359 (79%) 331 (15%) | 20 | −8 | −25 |
| Central parts of magnetosomes | Carboxy-methyldextran | MSR-1 | | | | | | |
| Central parts of magnetosomes | Citric acid | MSR-1 | 1 to 15 | 3.7 | 788 | 25 | −12 | −18 |
| Central parts of magnetosomes | Oleic acid | MSR-1 | 0.5 to 5 | 3.5 | 123 | 30 ND | −10 ND | −40 −10 |
| Central parts of magnetosomes | Oleic acid | MSR-1 | | | | | | |
| Central parts of magnetosomes | Silica | MSR-1 | Gel | | | | | |
| Central parts of magnetosomes | Silica | MSR-1 | Gel | 6.7 | 1986 (93%) 277 (7%) 235 (10%) | 39 | 20 | 5 |

TABLE 2-continued

| Sample type | Coating | Species | Size (nm) | pH | Sizes (%) | col1 | col2 | col3 |
|---|---|---|---|---|---|---|---|---|
| Parties centrales des magnetosomes | Folic acid | MSR-1 | 1 to 4 | 7.9 | 2876 (90%) 235 (10%) | 45 | 33 | 24.4 |
| Central parts of magnetosomes | Folic acid | MSR-1 | | | | | | |
| Central parts of magnetosomes | DOPC | MSR-1 | 0.6 to 3 | 3 | 1871 (87%) 278 (13%) | 10 | −6.5 | −16 |
| Central parts of magnetosomes | DOPC | MSR-1 | | | | | | |
| Central parts of magnetosomes | DOPC | AMB-1 | 50 à 150 | | | | | |
| Central parts of magnetosomes | Alendronate | AMB-1 | | | | | | |
| Central parts of magnetosomes | Alendronate | AMB-1 | Matrix | 3.5 | 2735 (86%) 527 (14%) | 25 | −7 | −30 |
| Central parts of magnetosomes | Neridronate | MSR-1 | 19 to 200 | 3.5 | 5560 (1%) 710 (59%) 207 (40%) | 40 | −7.9 | −26 |
| Central parts of magnetosomes | Neridronate | MSR-1 | | | | | | |
| Central parts of magnetosomes | PEI | MSR-1 | 8 to 10 | 11 | 175 | 42 | 39 | 37 |
| Central parts of magnetosomes | PEI | AMB-1 | 4 to 18 | | | | | |
| Central parts of magnetosomes | PEI | AMB-1 | 4 to 18 | 11.3 | 1067 (93%) 5445 (1%) 125 (6%) | 50 | 44 | 35 |
| Central parts of magnetosomes | Al(OH)$_3$ | MSR-1 | Gel | | | | | |
| Central parts of magnetosomes | Al(OH)$_3$ | MSR-1 | Gel | 2.5 | 1810 (95%) 204 (5%) | 5 | −7 | −16 |

| Sample properties | | | Zeta potential (mV) | | | CHNS analysis | | | |
|---|---|---|---|---|---|---|---|---|---|
| Sample type | Coating | Species | pH 8 | pH 10 | pH 12 | % N | % C | % H | % S |
| BNF-Starch | starch | | | | | | | | |
| BNF-Starch | Hydroxyethyl-starch | chemical | 5 | −3 | −20 | | 8.7 | | |
| Whole bacteria | | AMB-1 | | | | | | | |
| Whole bacteria | | AMB-1 | | | | | 32.0 | | |
| Whole bacteria | | MSR-1 | | | | 11 | 49 | | 0.4 |
| Pyrogenic extracted chains | Bacterial membrane | AMB-1 | −26 | −34 | −38 | | | | |
| Pyrogeinc extracted chains | Membrane bacterianne | AMB-1 | | | | | 13.9 | | |
| Pyrogenic extracted chains | Bacterial membrane | MSR-1 | | | | 0.7 | 4.1 | 0.7 | 0.4 |
| Pyrogenic extracted chains | Bacterial membrane | MSR-1 | −15 | −26 | −31 | | 12.2 | | |
| Central parts of magnetosomes | None | AMB-1 | −56 | −58 | −60 | | | | |
| Central parts of magnetosomes | None | AMB-1 | | | | | 4.9 | | |
| Central parts of magnetosomes | None | MSR-1 | −27 | −35 | −45 | 0.2 | 3.3 | 0.5 | 0.002 |
| Central parts of magnetosomes | Poly-L-lysine | MSR-1 | 5 | −14 | −34 | 0.4 | 3.6 | 0.6 | 0.03 |
| Central parts of magnetosomes | Chitosan | MSR-1 | | | | | | | |
| Central parts of magnetosomes | Chitosan | MSR-1 | 29 | 21 | −55 | | 3.2 | | |
| Central parts of the magnetosomes | Carboxy-methyldextran | MSR-1 | −30 | −31 | −31 | | | | |
| Central parts of magnetosomes | Carboxy-methyldextran | MSR-1 | | | | | 3.7 | | |

TABLE 2-continued

| | | | | | | | | | |
|---|---|---|---|---|---|---|---|---|---|
| Central parts of magnetosomes | Citric acid | MSR-1 | −27 | −31 | −38 | 0.8 | 3.7 | 0.3 | 0 |
| Central parts of magnetosomes | Oleic acid | MSR-1 | −50 −30 | −55 −35 | −60 −35 | | | | |
| Central parts of magnetosomes | Oleic acid | MSR-1 | | | | | 3.4 | | |
| Central parts of magnetosomes | Silica | MSR-1 | | | | | | | |
| Central parts of magnetosomes | Silica | MSR-1 | −10 | −25 | −31 | | 7.4 | | |
| Parties centrales des magnetosomes | Folic acid | MSR-1 | −0.2 | −32 | −43 | | | | |
| Central parts of magnetosomes | Folic acid | MSR-1 | | | | | 3.9 | | |
| Central parts of magnetosomes | DOPC | MSR-1 | −20 | −25 | −3.5 | | | | |
| Central parts of magnetosomes | DOPC | MSR-1 | | | | | 7.5 | | |
| Central parts of magnetosomes | DOPC | AMB-1 | | | | | | | |
| Central parts of magnetosomes | Alendronate | AMB-1 | | | | | | | |
| Central parts of magnetosomes | Alendronate | AMB-1 | −40 | −45 | −47 | | 9 | | |
| Central parts of magnetosomes | Neridronate | MSR-1 | −30 | −31 | −42 | | | | |
| Central parts of magnetosomes | Neridronate | MSR-1 | | | | | 18.1 | | |
| Central parts of magnetosomes | PEI | MSR-1 | 29 | 8 | −16 | 1.1 | 4.5 | 0.7 | 0 |
| Central parts of magnetosomes | PEI | AMB-1 | | | | | | | |
| Central parts of magnetosomes | PEI | AMB-1 | 26 | 12 | −10 | | 6.6 | | |
| Central parts of magnetosomes | Al(OH)$_3$ | MSR-1 | | | | | | | |
| Central parts of magnetosomes | Al(OH)$_3$ | MSR-1 | −23 | −26 | −30 | | 3.3 | | |

TABLE 3

| Coating | Bacteria species | Distance between the external surfaces of two central parts separated by binding material | | Number of central parts linked together by binding material | | Geometric shape |
|---|---|---|---|---|---|---|
| | | Min | Max | Min | Max | |
| PEI | MSR1 | 0 | 16 | 2 | 26 | Individual chains, chains sticked together, chains, spherical aggregates, circles. |
| PEI | AMB1 | 0 | 191 | 2 | 5 | Chains, circles |
| DOPC | MSR1 | 0 | 27 | 2 | 16 | Chains, circles diamond |
| Neridronate | MSR1 | 0 | 31 | 2 | 18 | Chains, chains sticked together |
| Chitosan | MSR1 | 0 | 11 | 2 | 42 | Chains, chains sticked together |
| Citric acid | MSR1 | 0 | 16 | 2 | 26 | Chaines, circles, triangle, quadrilateral |
| Dextran | MSR1 | 0 | 113 | 2 | 8 | Circles, chains |
| AlOH$_3$ | MSR1 | 0 | >200 nm | NA | >10000 | Chain, circle in a gel |
| Silica | MSR1 | 0 | >50 nm | NA | >10000 | Chain, circle in a gel |
| Folic acid | MSR1 | 0 | >400 nm | NA | >10000 | Chain, circle in a gel |

The invention claimed is:

1. A preparation comprising at least one synthetic nanoparticle, the at least one synthetic nanoparticle comprising:
   a crystallized mineral central part comprising predominantly an iron oxide, the central part having been produced by a living organism, and
   a coating comprising materials not produced by said living organism, the coating covering the central part completely or partly,
   wherein the coating does not comprise proteins produced by said living organism, and wherein the least one synthetic nanoparticle comprises less than 12% in mass of carbon produced by said living organism.

2. The preparation according to claim 1, wherein the living organism is a bacterium.

3. The preparation according to claim 1, wherein the central part comprises maghemite and/or magnetite.

4. The preparation according to claim 1, in which the at least one synthetic nanoparticle is non-pyrogenic.

5. The preparation according to claim 1, wherein the at least one synthetic nanoparticle comprises an endotoxin quantity, which abides by at least one quality or regulatory standard in force applicable to medical devices, drugs or cosmetic products, in particular conforming to a ISO quality standard or a current pharmacopoeia.

6. The preparation according to claim 1, wherein the coating of the at least one synthetic nanoparticle enables an arrangement in a chain of at least two synthetic nanoparticles, said at least two synthetic nanoparticles having crystallographic axes orientated in the direction of elongation of the chain.

7. The preparation according to claim 1, wherein the coating comprises at least one compound able to establish weak interactions or covalent bonds with the central part of the at least one synthetic nanoparticle.

8. The preparation according to claim 1, wherein the coating comprises at least one compound able to establish interactions or bonds with $Fe^{2+}$ or $Fe^{3+}$ ions, hydroxyls $OH^-$, oxides $O^{2-}$, or crystalline defects of the central part.

9. The preparation according to claim 1, wherein the coating comprises carbonaceous compounds.

10. The preparation according to claim 1, wherein the coating comprises at least one compound selected from the group consisting of a chelator, an amphipathic molecule, a polarized or charged polymer, a metal or silicon oxide, a hydroxide of a metal or silicon, an acid, an acidic, basic, oxidized, reduced, neutral, positively charged, negatively charged derivative of these compounds, and a combination of several of these compounds or derivatives.

11. The preparation according to claim 1, wherein the coating comprises at least one compound selected from the group consisting of a polysaccharide, a fatty acid, a phospholipid, a polymer of amino acids, polymeric or non-polymeric silica, and an aliphatic amino polymer, of an acidic, basic, oxidized, reduced, neutral, positively charged, negatively charged derivatives of these compounds and a combination of several of these compounds or derivatives.

12. The preparation according to claim 1, wherein the coating comprises at least one function selected from the group consisting of carboxylic acids, phosphoric acids, sulfonic acids, esters, amides, ketones, alcohols, phenols, thiols, amines, ether, sulfides, acid anhydrides, acyl halides, amidines, nitriles, hydroperoxides, imines, aldehydes, peroxides, of an acidic, basic, oxidized, reduced, neutral, positively charged, negatively charged derivative of these compounds, and a combination of several of these compounds or derivatives.

13. A method for treating a tumor in an individual or animal, wherein a therapeutically active quantity of the preparation according to claim 1 is administered to the individual or animal.

14. A pharmaceutical composition or drug comprising, as active principle, a preparation as defined in claim 1 and optionally at least one pharmaceutically acceptable carrier.

15. A medical device comprising a preparation as defined in claim 1.

16. A diagnostic composition comprising a preparation as defined in claim 1.

17. A cosmetic composition comprising, as cosmetic active principle, a preparation as defined in claim 1.

18. A method for the manufacture of a preparation as defined in claim 1, comprising the following steps:
(i), from a preparation of nanoparticles synthesized by a living organism comprising a crystallized central part composed predominantly of an iron oxide and a biological coating, isolating the central part;
(ii), treating the resulting isolated central part to cover the central part with a coating;
(iii), optionally sterilize the preparation, after step (i) or after step (ii).

19. The preparation according to claim 1, wherein the central part is synthesized by a magnetotactic bacterium.

20. The preparation according to claim 1, wherein the central part has a size comprised between 1 nm and 2 µm.

21. The preparation according to claim 1, wherein the less than 12% in mass of carbon produced by said living organism are comprised in carbonaceous material.

22. The preparation according to claim 1, wherein the coating has a thickness larger than 0.1 nm.

23. The preparation according to claim 9, wherein the at least one synthetic nanoparticle is prepared by a process comprising the steps of:
obtaining or starting from at least one natural nanoparticle produced by a living organism, the at least one natural nanoparticle comprising a crystallized mineral central part that comprises predominantly an iron oxide and an original coating that covers the central part;
removing from the central part at least a portion of the original coating such that the central part is associated with less than 12% in mass of carbon and with no proteins originating from the living organism that produced the central part; and
applying a new coating not produced by the living organism to the central part from which the at least a portion of the original coating has been removed, the new coating covering the central part completely or partly, to form the at least one synthetic nanoparticle, which comprises less than 12% in mass of carbon originating from the living organism that produced the central part and no proteins originating from the living organism that produced the central part.

* * * * *